(12) United States Patent
Gay

(10) Patent No.: US 12,017,228 B2
(45) Date of Patent: Jun. 25, 2024

(54) DEVICE HAVING MULTIPLE STERILE FLUID PATHS INTEGRATED ONTO A DISPOSABLE CONTAINER

(71) Applicant: Sartorius Stedim Biotech GmbH, Göttingen (DE)

(72) Inventor: Isabelle Gay, Peypin (FR)

(73) Assignee: Sartorius Stedim Biotech GmbH (DE)

( * ) Notice: Subject to any disclaimer, the term of this patent is extended or adjusted under 35 U.S.C. 154(b) by 647 days.

(21) Appl. No.: 16/634,126

(22) PCT Filed: Jun. 13, 2018

(86) PCT No.: PCT/EP2018/065581
§ 371 (c)(1),
(2) Date: Jan. 24, 2020

(87) PCT Pub. No.: WO2019/057354
PCT Pub. Date: Mar. 28, 2019

(65) Prior Publication Data
US 2020/0206744 A1    Jul. 2, 2020

(30) Foreign Application Priority Data
Sep. 22, 2017   (EP) .................................... 17290123

(51) Int. Cl.
*C12M 3/00*       (2006.01)
*B01L 3/00*       (2006.01)
(Continued)

(52) U.S. Cl.
CPC ............. *B01L 3/563* (2013.01); *C12M 23/28* (2013.01); *C12M 23/40* (2013.01); *C12M 23/46* (2013.01);
(Continued)

(58) Field of Classification Search
CPC ................................ C12M 23/28; B01L 3/563
See application file for complete search history.

(56) References Cited

U.S. PATENT DOCUMENTS 6,032,543 A     3/2000  Arthun
7,282,176 B2 * 10/2007  Glachet .................... B01L 1/02
                                                422/26

(Continued)

FOREIGN PATENT DOCUMENTS

DE        199 06 514      8/1999
DE     10 2006 005533     8/2007
(Continued)

OTHER PUBLICATIONS

English translation of DE 19906514, generated 2022.*
(Continued)

*Primary Examiner* — Nathan A Bowers
(74) *Attorney, Agent, or Firm* — Klarquist Sparkman, LLP

(57) ABSTRACT

Systems and a method for transferring chemical, pharmaceutical, and/or biological material into or out of a container are provided. One system comprises a disposable container having at least one port for accessing the interior of the container, the port comprising at least one connecting protrusion extending parallel to the container. The system further comprises a transfer interface connectable to the port. The transfer interface comprises a plate, and at least one connecting flange extending from the plate, the connecting flange to be arranged under the respective connecting protrusion to connect the transfer interface to the port, such that when the transfer interface is connected to the port the plate is parallel to a surface of the container.

14 Claims, 16 Drawing Sheets

(51) Int. Cl.
*C12M 1/00* (2006.01)
*C12M 1/26* (2006.01)

(52) U.S. Cl.
CPC ............ *C12M 27/18* (2013.01); *C12M 33/00* (2013.01); *B01L 2200/141* (2013.01); *B01L 2400/00* (2013.01)

(56) References Cited

U.S. PATENT DOCUMENTS

| | | |
|---|---|---|
| 8,539,988 B2 | 9/2013 | Guedon |
| 9,120,585 B2 | 9/2015 | Olivier |
| 9,920,841 B2 | 3/2018 | Saragosa |
| 2004/0005259 A1* | 1/2004 | Sacca ........................ A61L 2/26 422/298 |
| 2014/0103077 A1 | 4/2014 | Zumbrum |
| 2015/0345689 A1 | 12/2015 | Selker et al. |
| 2016/0298068 A1 | 10/2016 | Schumacher et al. |

FOREIGN PATENT DOCUMENTS

| | | |
|---|---|---|
| EP | 2 738 399 | 6/2014 |
| EP | 2 829 598 | 1/2015 |
| WO | WO 00/66706 | 11/2000 |
| WO | WO 2011/071897 | 6/2011 |

OTHER PUBLICATIONS

International Search Report and Written Opinion, dated Nov. 26, 2018, from PCT Application No. PCT/EP2018/065581, 22 pages.
Extended European Search Report, dated Jul. 9, 2018, from EP Patent Application No. 17290123.3, 15 pages.

\* cited by examiner

DEVICE HAVING MULTIPLE STERILE FLUID PATHS INTEGRATED ONTO A DISPOSABLE CONTAINER

CROSS REFERENCE TO RELATED APPLICATIONS

This is the U.S. National Stage of International Application No. PCT/EP2018/065581, filed Jun. 13, 2018, which was published in English under PCT Article 21(2), which in turn claims the benefit of European Application No. 17 290 123.3, filed Sep. 22, 2017. The prior applications are incorporated herein by reference in their entirety.

The technical field of the present application is the transfer of chemical, pharmaceutical, and/or biological material into or out of a container, such as a bioreactor. More specifically, aspects of the application relate to a disposable container, such as a disposable bioreactor, and a transfer interface connectable to a port of the disposable container.

Chemical, pharmaceutical, or biological material may be in the form of a fluid, such as a solution or a suspension. The (disposable) container may be a bioreactor (e.g., a fermenter), a mixer, a storage container or any other type of container used for fluid management in pharmaceutical and bioprocess industries. The container may be used for culturing cells or microorganisms. For example, the container may be used in culturing one or more of the following: bacteria, fungi, algae, plant cells, animal cells, protozoans, nematodes. Further, the container may accommodate cells and microorganisms that are aerobic, anaerobic, adherent or non-adherent. The system of the present application can also be used in the production of media, chemicals, food products, medicines, beverages, and other liquid products.

The disposable container may also be referred to as a single-use container or a single-use vessel (e.g., a single-use bioreactor). A majority of the components of the disposable container that contact the material inside the container may be disposed of after use. Use of disposable containers may substantially eliminate the burden of cleaning and sterilization required when using standard stainless steel equipment. Moreover, sterility can be easily and consistently maintained in the disposable container during repeated processing of multiple batches of chemical, pharmaceutical, or biological material.

The disposable container has at least one port for accessing the interior or inside of the container. The port may also be used for accessing the contents of the container. According to one example, the disposable container includes a chamber, and the at least one port includes an inlet port and an outlet port.

The at least one port may have a variety of uses. In particular, the port may deliver controlled volumes of fluid to the interior of the container. Further, ports may be used for extracting or sampling material, such as fluid, from the container or inserting probes, such as a temperature probe, to monitor conditions within the disposable container.

Periodic sampling of the contents of a container may be carried out in order to ensure that development of the contents is proceeding as desired. Further, it may be desirable to ensure that such sampling is carried out in a sterile manner, i.e., without having a negative effect on the contents of the container.

The disposable container may be manufactured from polymeric materials. In particular, the disposable container may be manufactured from fluoropolymers, or thermoplastics such as, polypropylene, polystyrene, polyethylene, Etlylene-Vynil Acetate, or polyurethane. The disposable container may also be made from layers of different materials, e.g., one layer of polyethylene and a second layer of polyamide. Other materials may also be used.

The disposable container may be sterilized before use with gamma radiation, steam, and/or aggressive chemicals such as ethylene oxide. Other sterilization methods may also be used. The disposable container may have various sizes, shapes, and configurations. For example, the disposable container may include a chamber having a capacity of at least 10 liters, 30 liters, 50 liters, 100 liters, 250 liters, 500 liters, 750 liters, 1000 liters, 1500 liters, or 3000 liters. Other volumes are also possible. According to one example, the disposable container may have a capacity of between 10 liters and 3000 liters, or between 50 liters and 2000 liters.

The disposable container may include a variety of components for processing chemical, pharmaceutical, or biological material. In particular, the disposable container may include one or more of the following: an impeller, a conductivity sensor, a thermowell. The disposable container may be at least partially filled with chemical, pharmaceutical, or biological material. The interior or chamber of the disposable container may be inflated. The disposable container may be made from a flexible, e.g. film, material. More specifically, the disposable container may have flexible walls. In particular, the disposable container may include a pre-sterilized, plastic bag. In some cases, the disposable container could be rigid, e.g. rigid thermoplastic, glass, or metal.

According to an aspect, a system for transferring chemical, pharmaceutical, and/or biological material into or out of a container is provided. The system comprises a disposable container having at least one port for accessing the interior of the container. The system further comprises a transfer interface connectable to the at least one port. The transfer interface comprises a plurality of extensible transfer elements for extracting one or more samples from the disposable container, preferably in a sterile manner.

The transfer elements may also be referred to as extracting elements, sampling elements, extractors, or probes. Each of the transfer elements has a corresponding biasing element for retracting the transfer element. The transfer interface further comprises a locking mechanism for locking one of the transfer elements such that the locked transfer element cannot be extended. Each of the transfer elements may have a corresponding locking mechanism. The biasing element may be implemented as a spring or as another device capable of applying a biasing force.

The transfer interface may be implemented as a fluid transfer interface. Unless otherwise indicated (e.g., via the term "multi-use"), the term "transfer interface" refers to a transfer interface for use with the disposable container. The transfer interface may be referred to as a sampling device.

The term "sterile manner" is used in the sense that transfer (e.g., fluid transfer) is performed aseptically. Accordingly, samples can be extracted or substances can be added to the disposable container in a process that is free from contaminants, such as microorganisms (e.g., bacteria, viruses or other exogenous microbes). Thus, during use of the transfer interface microorganisms (e.g., germs) or substances are prevented from getting from the outside into the interior of the container.

In some cases, extracting samples of material from the container in a sterile manner is carried out by ensuring one or more of the following:
the transfer elements are pre-sterilized,
the transfer elements remain sterilize until used.

Transfer elements may be repeatedly used as long as sterility is maintained. For example, testing has shown that some transfer elements remain sterile for up to 40 uses (e.g., 40 separate extractions of material from the container, 20 extractions and 20 insertions/additions, etc.).

At least one transfer element may include a sharp instrument, such as a needle. The needle may be hollow. More particularly, the transfer element may be implemented as a cannula, i.e., a flexible tube containing a sharp instrument (e.g. a trocar needle) at one end. The tube of the cannula may surround the inner or outer surface of the sharp instrument, thereby extending the effective length of the instrument by at least about 50% of its original length.

The transfer element may be used to extract or collect samples from the container, e.g. by extracting material, such as a fluid, contained within the container. Further, the transfer element can be used to introduce a material or substance into the container. The transfer elements of the transfer interface may collect samples from the container by connecting to a port of the container and extracting chemical, pharmaceutical, or biological material from the container via the port.

The locking mechanism may lock one of the transfer elements after the transfer element has collected a sample from the container.

The locking mechanism may be used to ensure that transfer elements that have already been used are not reused.

The transfer interface may further comprise a septum or membrane. The transfer elements may extend axially (i.e., substantially parallel to the long axis or lengthwise) along the interior of the transfer interface. In order to collect samples from the disposable container, the transfer elements may extend beyond the septum. In particular, the transfer elements may pierce or breach the septum in order to collect samples from the container. The transfer elements may retreat behind the septum when retracted. In particular, the transfer elements may extend and retract along the longitudinal axis of the transfer interface.

The septum may be used to ensure that the transfer elements remain sterile until use.

After one of the transfer elements retracts behind the septum, the septum may reseal, i.e., sterile extraction may again be possible using the same transfer element. A side of each transfer element may include a hole for fluid transfer. Accordingly, each one of the transfer elements may include a hole on its side, between the middle of the transfer element and a tip of the transfer element, where the tip extends into the container. For example, if a distance between the middle of the transfer element and the tip of the transfer element is X, the hole may be located about one fourth (or about one fifth) of X from the tip of the transfer element. The hole may be perpendicularly situated from the tip of the transfer element.

Locating the hole of the side of the transfer element and transferring fluid through the hole may have the effect of preventing the transfer element from coring the septum.

In addition, the transfer interface may include a guide for guiding transfer elements along the same path during each actuation and retraction. The transfer interface may include a guide for each transfer element.

The transfer interface may further comprise a plate covering the septum, the plate having holes or apertures corresponding to each of the transfer elements. In particular, a transfer element may pass through its corresponding hole as it extends and retreat within the hole when it retracts. Each of the holes may be covered by the septum, such that a part of the septum covering the hole is pierced or breached when the transfer element corresponding to the hole extends.

The plate may be located between the septum and the container when the transfer interface is connected to the at least one port. The plate may be made of metal, such as steel. According to one example, when an transfer element extracts or collects a sample from the disposable container, the transfer element passes through the septum and extends beyond the septum and the plate.

The at least one port may be a plurality of ports. The at least one part may include a sensor port for arranging a sensor on the container in order to sense at least one parameter of the content of the container. The sensor port may be or comprise a pH port for measuring a relative amount of hydrogen and/or hydroxide ions within the container. The sensor may be attached to a wall of the container. Additionally or alternatively, the sensor may access the content of the container via a tube protruding from the sensor port into the container.

The transfer interface may comprise a grip. The grip may have an ergonomic shape, such as a crescent shape. The grip may be arranged such that the tips of the crescent protrude from opposing sides of the transfer interface. The longitudinal axis of the grip may be substantially perpendicular to the longitudinal axis of the transfer interface. The grip may be detachable.

The transfer interface may further comprise a switch. Activation of the switch may cause one of the transfer elements to extend from the transfer interface (i.e. beyond the plate) to collect a sample from the container. Deactivation of the switch may cause the extended transfer element to retract into the transfer interface. The switch may be referred to as an actuator, and may be implemented as a button. In one example, activation of the switch may occur when a user presses a button on the transfer interface. Deactivation of the switch may occur when the user releases the button.

The locking mechanism may be triggered to lock the transfer element upon activation of the switch. For example, the user may activate the switch to cause the transfer element to extend from the transfer interface to collect material (e.g., a sample from the disposable container).

The user may toggle the switch to cause the activation of the switch, which in turn causes the extended transfer element to retract. The retracted transfer element is then locked. Accordingly, it will no longer be possible to cause the locked transfer element to extend, even upon a repeated activation of the switch. In particular, further (or repeated) activation of the switch may cause another one of the transfer elements to extend from the transfer interface to collect a sample from the container. In some cases, e.g. when all the transfer elements have already been used to collect samples from the container, further activation of the switch will not result in extension of an transfer element to collect samples from the container.

The transfer interface may be connectable to the at least one port via a fastening means, possibly designed to be non-removable. The fastening means may be implemented using a bayonet connection, a sanitary clamp, a screw system or a snapping system between the transfer interface and the port may be implemented via a fastening mechanism. The fastening mechanism may consist of a cylindrical male side with one or more radial pins, and a female receptor with matching L-shaped slots along with one or more biasing elements (e.g., springs) to keep to two parts locked together.

The transfer interface may comprise a body including the transfer elements. The transfer interface may further comprise a plurality of tubes extending away from the body and the transfer elements. In particular, there may be a tube corresponding to each one of the transfer elements. The tube may be attached to an end of its corresponding transfer element opposing the plate. In other words, the plate is on (or near) one end of the body of the transfer interface and the tube is attached to an transfer element at the other end. The ends are referred to with regard to the longitudinal axis of the transfer interface. Further, the tube may extend from the end of the transfer element away from the other components of the transfer interface.

The system may further comprise a housing. The container may be provided within the housing and the housing may support the container. The housing may be made from a rigid plastic (e.g., thermoplastic, rigid nylon or rigid PVC) or metal, such as stainless steel.

A mounting bracket may be attached to the housing. For example, components of the mounting bracket may be arranged in front of the at least one port so as to support the transfer interface when the transfer interface is connected to the port.

The housing may comprise an opening for accessing the container. In particular, the opening may be sized so that the ports of the container can be accessed and other parts of the container cannot be accessed. In other words, the housing may cover portions of the container other than the ports. The mounting bracket may be arranged in front of or over the opening.

According to another aspect, a method for configuring a system to transfer chemical, pharmaceutical, and/or biological material into or out of a container is provided. The method comprises providing a disposable container having at least one port. The at least one port is suitable for accessing the interior of the container. The method may further comprise connecting a transfer interface to the at least one port, the transfer interface comprising a plurality of transfer elements. The method further comprises extending one of the transfer elements from the transfer interface to the container to collect a sample from the container in a sterile manner. The method further comprises retracting the extended transfer element from the container by means of a biasing element corresponding to the extended transfer element. The method further comprises locking the transfer element such that the transfer element cannot be extended. In some cases, the locking step occurs after the retracting step. It is also possible that the locking and retracting steps are carried out at the same time or that the locking step is carried out while the retracting is ongoing.

According to yet another aspect, a use of a transfer interface for accessing the interior of a disposable container is provided. The transfer interface comprises a plurality of extendible transfer elements for collecting samples from the disposable container in a sterile manner. Each of the transfer elements has a corresponding biasing element for retracting the transfer element. The transfer interface further comprises a locking mechanism for locking one of the transfer elements such that the locked transfer element cannot be extended. In some cases, distinct locking mechanisms may be provided for locking each transfer element or one locking mechanism may be provided for locking all of the transfer elements. The transfer interface is to be connected to at least one port of the disposable container.

According to a further aspect, a system for transferring chemical, pharmaceutical, and/or biological material into or out of a container is provided. The system comprises a disposable container having at least one port for accessing the interior of the container. The port comprises at least one connecting protrusion extending parallel to the container, i.e., parallel to an exterior surface of the container. The system further comprises a transfer interface connectable to the port. The transfer interface comprises a plate. The transfer interface further comprises at least one connecting flange extending from the plate. The connecting flange may be arranged under the respective connecting protrusion to connect the transfer interface to the port such that when the transfer interface is connected to the port the plate is parallel to a surface of the container when the transfer interface is connected to the port.

The arrangement of the connecting flange and the connecting protrusion may have the effect of keeping (holding) the transfer interface in place when the transfer interface is connected to the port. In particular, the connecting flange and the connecting protrusion may hinder or prevent a deformation of the transfer interface, such that the plate remains parallel to a surface (i.e., an exterior surface) of the container.

The plate may be adapted to conform to the surface of the container. When the transfer interface is connected to the port, the plate may at least partly contact the surface of the container. In some cases, the plate may be substantially flush with the surface of the container when the transfer interface is connected to the port.

The arrangement of the connecting flange and the connecting protrusion (in addition to the shape of the plate) may also help ensure that the plate remains parallel to the surface of the container when the transfer interface is connected to the port.

Alternatively, the plate may be opposite an opening in the container, such that the plate does not contact the surface of the container. Accordingly, the arrangement of the connecting protrusion and the connecting flange may ensure a sterile connection between the transfer interface and the port by keeping the plate parallel to the surface of the container (e.g., the exterior surface extending away from the opening).

In some cases, the port further comprises at least one stopping protrusion extending away from the container. Accordingly, the connecting protrusion may extend inward (i.e., toward the center of the port) from the stopping protrusion. The system may further comprise at least one stopping flange extending from the transfer interface. The stopping flange may be located between the plate and an end of the transfer interface opposite the plate.

The stopping flange may abut the stopping protrusion when the transfer interface is connected to the port. The term "abut" may be understood in the sense of contact and/or support. In other words, the stopping flange may contact or support the stopping protrusion when the transfer interface is connected to the port.

The stopping flange may comprise an extending portion and a flat portion. The extending portion may extend radially outward from the flat portion. The stopping protrusion may comprise an extending part and a parallel part. The extending part may extend away from the container. The parallel part may extend in a direction parallel to the surface of the container. The parallel part may be parallel to the connecting protrusion. The parallel part may be spaced further away from the container than the connecting protrusion.

When the transfer interface is connected to the port, the extending portion may abut the parallel part of the stopping protrusion and the flat portion may abut the extending part of the stopping protrusion.

In the context of the present application, abut may be understood as contact or touch.

The arrangement of the stopping flange and the stopping protrusion may have the effect of keeping the plate parallel to the surface of the container, when the transfer interface is connected to the port, and hindering or preventing deformation of the transfer interface. In particular, the extending part may support the flat portion, even when pressure is exerted on the transfer interface, e.g., in view of the weight of the transfer interface (possibly combined with the weight of material to be transferred) and/or user handling of the transfer interface.

The combination of the arrangement of the stopping protrusion and the stopping flange with the arrangement of the connecting protrusion and the connecting flange may be particularly effective for keeping the plate parallel to the surface of the container and hindering deformation of the transfer interface.

The stopping protrusion may extend radially away from the container. In some cases, at least part of a circumference of the stopping protrusion is not covered by the connecting protrusion. The stopping protrusion may have the form of a hollow cylinder. The parallel part of the stopping protrusion may be further from the surface of the container than any other part of the stopping protrusion.

The stopping protrusion may be a right circular cylinder. Alternatively, the stopping protrusion may be an elliptic cylinder.

The stopping flange may extend radially outward from the transfer interface. The stopping flange may cover the entire circumference of the transfer interface. In other words, the stopping flange may form a complete ring extending from the transfer interface.

The connecting flange may extend radially outward from the plate. In some cases, at least part of a circumference of the transfer interface is not covered by the connecting flange. The connecting flange may be in contact with the surface of the container when the transfer interface is connected to the port.

In some cases, an O-ring may be located between the connecting flange and the stopping flange. Accordingly, the system may further comprise two internal flanges located between the connecting flange and the stopping flange. Each internal flange may extend radially outward from the transfer interface. Each internal flange may cover the entire circumference of the transfer interface. For example, when the transfer interface is shaped like a right circular cylinder, each internal flange may form a complete circle extending radially from the surface of the cylinder.

The O-ring may be located between the two internal flanges. The O-ring may be supported by the two internal flanges.

The port may comprise a port flange. The port flange may be attached to the disposable container. In particular, the port flange may be glued or welded to the disposable container.

The O-ring may be colored such that the O-ring is visible from outside the transfer interface. For example, the O-ring may be brightly colored so that a user can see that the O-ring is correctly positioned.

The connecting flange and the connecting protrusion may be parts of a bayonet connection to connect the transfer interface to the port.

The stopping protrusion may stop progress of the transfer interface toward the container. The stopping protrusion may also help prevent deformation of the transfer interface and keep the plate parallel to the surface of the container, as described above.

There may be two connecting flanges, a first gap, and a second gap. The two connecting flanges may extend around different parts of the circumference of the plate. The two connecting flanges may be diametrically opposed. The two gaps may be diametrically opposed.

The system may further comprise a holder for supporting the transfer interface when the transfer interface is connected to the port. The holder may be attachable to one or more of the following: the transfer interface, the port.

The holder may be made of metal, e.g. aluminum. Alternatively, the holder may be made from a plastic, e.g., a flexible plastic and/or a thermoplastic.

The holder may comprise an attachment for the transfer interface in the shape of a ring or a horseshoe.

The holder may comprise lateral extensions that contact the surface of the container when the transfer interface is connected to the port. The lateral extensions may support the transfer interface via the attachment for the transfer interface. In other words, the weight of the transfer interface may be transferred through the attachment and distributed to the container via the lateral extensions. The lateral extensions may be referred to as wings.

The holder may help keep the plate parallel to the surface of the container when the transfer interface is connected to the port. Moreover, the holder may hinder or prevent deformation of the transfer interface, e.g., resulting from the weight of the transfer interface or use of the transfer interface.

The combination of two arrangements and the holder may be very effective at keeping the plate parallel to the surface of the container and hindering deformation of the transfer interface. In particular, the combination of the arrangement of the connecting flange and the connecting protrusion, the arrangement of the stopping flange and the stopping protrusion, as well as the holder may work together to hinder or prevent deformation of the transfer interface and ensure that the plate remains parallel to the surface of the container when the transfer interface is connected to the port. The combination may keep the plate parallel to the surface of the container in spite of the weight of the transfer interface and/or continued use of the transfer interface.

According to an additional aspect, a system for transferring chemical, pharmaceutical, and/or biological material into or out of a container, such as a bioreactor, is provided. The system comprises a disposable container having at least one port for accessing the interior of the container. The port comprises a supporting protrusion. The system further comprises a transfer interface connectable to the port.

The transfer interface comprises a plate. The supporting protrusion supports the transfer interface and extends from the surface of the container along at least 25% of the length of the transfer interface, such that the plate is parallel to (e.g., flush with) a surface of the container when the transfer interface is connected to the port.

The system may further comprise a triclamp for connecting the transfer interface to the port. The triclamp may be one of the following:
integrated with the transfer interface,
integrated with the port,
separate from the transfer interface and the port.

According to another aspect, a method for configuring a system to transfer chemical, pharmaceutical, and/or biological material into or out of a container, such as a bioreactor, is provided. The method may comprise providing a disposable container having at least one port. The at least one port is suitable for accessing the interior of the container. The port comprises at least one connecting protrusion extending parallel to the container. The method further comprises connecting a transfer interface to the port. The transfer interface comprises a plate. The plate may be adapted to conform to a surface of the container. At least one connecting flange extends from the plate. The connecting may comprise arranging the connecting flange under the connecting protrusion such that the plate is parallel to (e.g., flush with) the surface of the container. The connecting may result in a sterile connection between the transfer interface and the port.

When there are multiple connecting flanges and connecting protrusions, the connecting may comprise arranging the respective connecting flange under the respective connecting protrusion.

DETAILED DESCRIPTION

In the following text, a detailed description of examples will be given with reference to the drawings. It should be understood that various modifications to the examples may be made. In particular, one or more elements of one example may be combined and used in other examples to form new examples.

Figure 1:
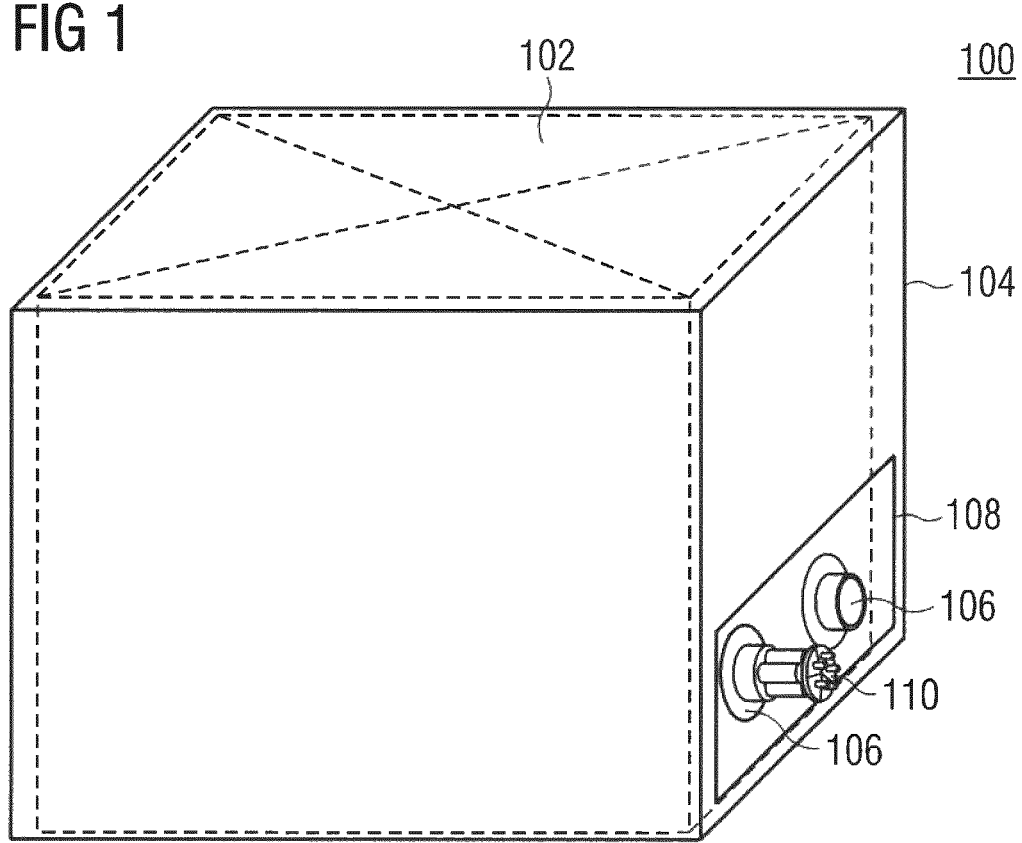
FIG. 1 shows a housing, a disposable container provided within the housing, and a transfer interface connected to a port of the container.

FIG. 1 shows a system 100 for transferring chemical, pharmaceutical, and/or biological material into or out of a disposable container 102, such as a bioreactor. The system includes the disposable container 102 within a housing 104.

The disposable container 102 has at least one port 106 for accessing the interior of the container 102. The housing 104 includes at least one opening 108 for accessing the at least one port 106. The at least one port 106 may be a sensor port, such as the pH port. Although only one port is shown, it should be understand that the disposable container 102 may have multiple ports, e.g., more than three ports.

The port 106 may be connected to the container 102. In particular, the port 106 may be adhered or welded to the container 102.

A transfer interface 110 can be connected to the at least one port 106. The transfer interface 110 may be used to collect samples from the disposable container 102 in a sterile manner. In particular, components of the transfer interface 110 and the disposable container 102 may be pre-sterilized before use. The sterilization/pre-sterilization may be carried out via gamma irradiation, steam, electron beam processing (also referred to as electron irradiation) and/or aggressive chemicals.

Some sterilization methods may not be suitable depending on the composition of the container 102 or the transfer interface 110.

It may be desirable to collect the samples in such a way that they reflect the content of the container 102 as a whole. In other words, the content of the collected samples should be homogenous with the content of the container 102, and not heterogeneous with the content of the container 102.

The disposable container 102 may have at least one port 106 for accessing the material contained within the container 102. The container 102 may be a flexible, single-use bag, e.g., a plastic film. The container 102 could also be semi-rigid, or rigid. For example, the container 102 may be made from a rigid thermoplastic. Alternatively, the container 102 may be made from metal.

The disposable container 102 may be supported by the housing 104. The housing 104 may be made from metal, such as stainless steel. Other materials are also possible. The housing 104 may be reusable. The opening 108 in the housing 104 may be referred to as a window. The opening 108 may be large enough so that the port 106 can be accessed but small enough so as to minimize exposure of the container 102. Further, the size of the opening 108 may be minimized in order to maximize the support of the container 102 provided by the housing 104.

The transfer interface 110 may be connected to the port 106 in such a way that the transfer interface 110 cannot be disconnected, e.g., in order to preserve the sterility of the container 102. In other words, the transfer interface 110 may be permanently connected to the container 102.

Alternatively, the transfer interface 110 may be connected to the container 102 and disconnected from the container 102. Thus, the transfer interface 110 may be detachably connected to the container 102. The transfer interface 110 may be disposable or reusable after sterilization. Disposing of the transfer interface 110 after use, e.g., after each of the transfer elements have been used, may have the advantage of making use (e.g., sterilization) of the transfer interface 110 easier.

The samples or specimens collected via the transfer interface 110 may be fluid. The transfer interface 110 may also be used to insert or inject chemical, pharmaceutical, or biological material into the container 102.

Figure 2:
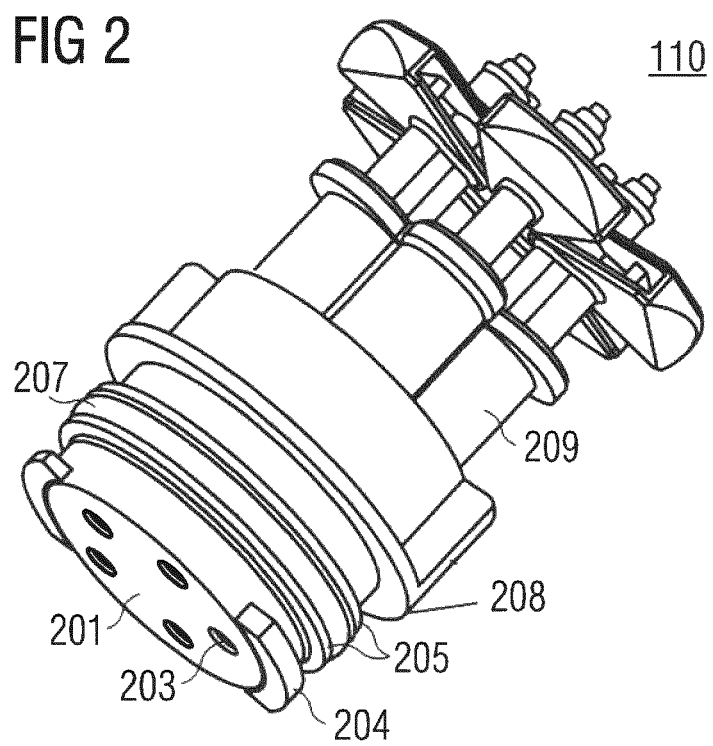
FIG. 2 shows the transfer interface.

Once the transfer interface 110 is detachably connected to the port 106, material may be removed from the container 102 without exposing the material to the atmosphere. In particular, a seal may be established between the transfer interface 110 and the disposable container 102. The seal may be established via a bayonet connection between the transfer interface 110 and the port 106. The seal may facilitate extraction of material from the container 102 in a sterile manner. The seal may be facilitated via an O-ring 207, as shown in FIG. 2. In particular, the O-ring 207 may help create the seal between the transfer interface 110 and the port 106.

The bayonet connection may provide a particularly secure fit and help ensure sterility (e.g., ensure that undesired microorganisms do not enter the container 102) despite repeated use of the transfer interface 110.

FIG. 2 depicts the transfer interface 110. The transfer interface 110 may comprise a body including a plurality of extendible transfer elements, and a plate 201 having a plurality of holes 203. FIG. 2 shows five holes in the plate 201, however, there may be more or fewer holes 203. The holes 203 may have a shape that allows passage of an extendible transfer element through the plate 201. For example, the holes 203 may be round.

The plate 201 may cover a septum. At least one connecting flange 204 may project out from the transfer interface 110 on the plane of the plate 201. For example, two connecting flanges 204 may project out from the transfer interface 110. The connecting flanges 204 may be diametrically opposed. In particular, the transfer interface 110 may have a substantially cylindrical shape. The plate 201 may be at one end of the transfer interface 110. Two internal flanges 205 may be located between the plate and the other end of the transfer interface 110.

There may be another O-ring (not shown) between the plate 201 and the connecting flange 204, to form a seal between the plate 201 and the connecting flange 204.

Distribution tubes 401 (see FIG. 4) may extend from the other end of the body of the transfer interface 110. The distribution tubes 401 may be connected to containers for holding samples extracted from the disposable container 102. An O-ring 207 may be fitted around the transfer interface 110. According to the example in FIG. 2, the O-ring 207 is between the two internal flanges 205. The connecting flange 204 may be part of the bayonet connection between the transfer interface 110 and the at least one port 106.

The O-ring 207 may be referred to as a gasket or a sealing ring. The O-ring 207 may be colored. In particular, the O-ring 207 may be brightly colored and visible through the transfer interface 110. Coloring of the O-ring 207 may make it possible to ensure that the O-ring 207 is present and in a correct position. The O-ring 207 may be made from synthetic or natural rubber, thermoplastic, or another elastic or pliable material.

The connecting flange 204 may be rotated underneath a corresponding protrusion (e.g., a connecting protrusion 1201, see FIG. 12A below) of the port 106. The connecting flange 204 may support the transfer interface 110 when the transfer interface 110 is connected to the port 106. Once the transfer interface 110 is connected to the port 106, the plate 201 may be parallel to a corresponding surface of the container 102.

In some cases, upon connection of the transfer interface 110 to the port 106, the plate 201 may be substantially flush the corresponding surface of the container 102. In other cases, the plate 201 may be arranged opposite an opening in the container 102.

Figure 12A:
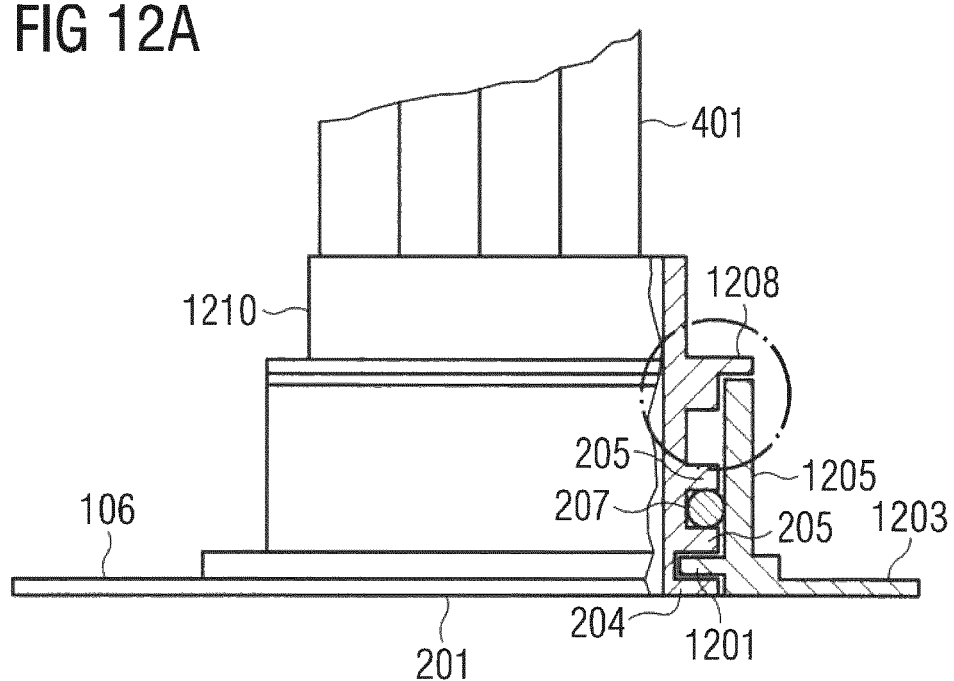
FIG. 12A shows a connection between another transfer interface and the port of the disposable container.

A stopping flange 208 may press against or be substantially flush with the port 106 when the transfer interface 110 is connected to the container 102. In particular, the stopping flange 208 may extend to a part of the port 106 to keep the transfer interface 110 parallel to the surface of the container 102 and prevent potential deformation of the walls of the port 106 (for example, to maintain the port 106 in a cylindrical shape). Such deformation may lead to a leak. For example, the stopping flange 208 may contact a stopping protrusion 1205, as shown in FIG. 12A below.

A containing tube 209 may contain one of the extendible transfer elements. The transfer element may be used for collecting samples from the disposable container 102. The transfer element may pass through the hole 203 in order to collect the sample and then retract behind the plate 201 once the sample has been retrieved. A biasing element may bring about retraction of the transfer element. In particular, the biasing element may apply a biasing force along the longitudinal axis of the transfer interface 110 to pull the transfer element away from the port 106.

The transfer element may comprise a sharp, hollow needle. In particular, the transfer element may be a cannula. The septum may be a soft, flexible membrane made from organic or inorganic material. For example, the septum may be made from an elastomer, such as a silicone elastomer, a fluoro elastomer, or a perfluoropolyether elastomer. In particular, the septum may be made from platinum-cured silicone.

The septum may have a cylindrical shape with a diameter of about 12.5-13.5 mm (e.g., 12.9 mm) and a height of about 2-3 mm (e.g., 2.5 mm).

Figure 3:
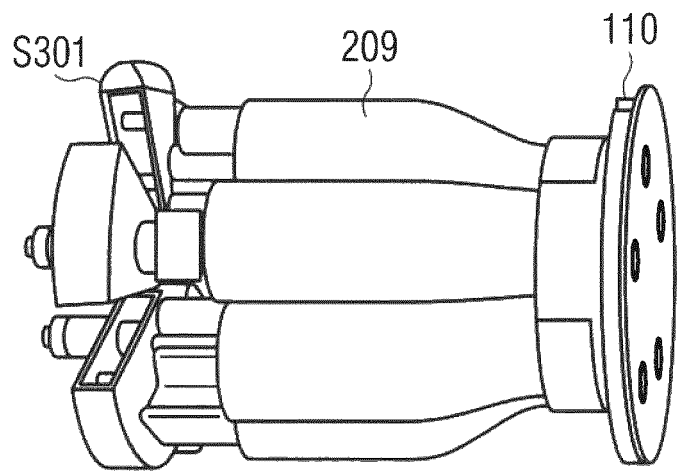
FIG. 3 shows the transfer interface before, during, and after extension of an transfer element.
Figure 3:
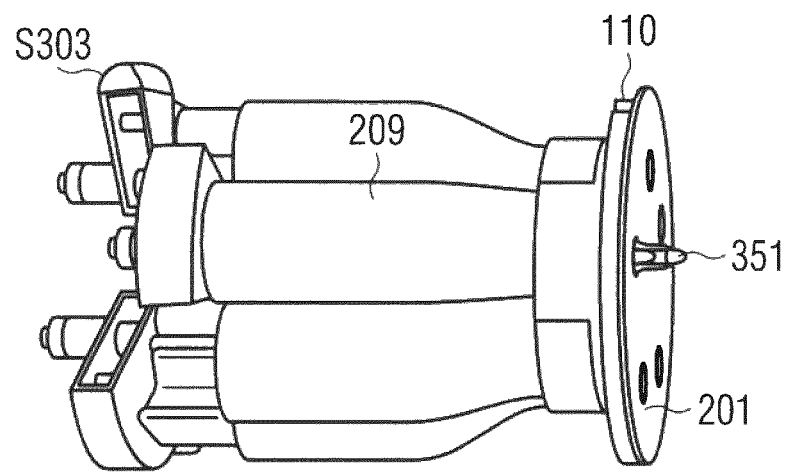
Figure 3:
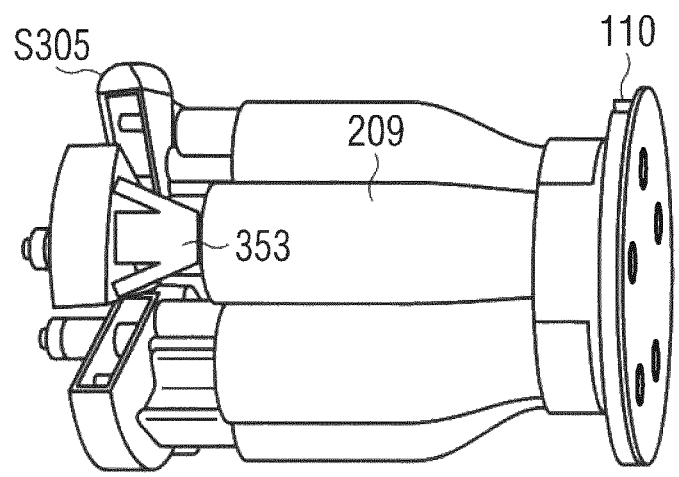

FIG. 3 shows functionality of a locking mechanism 353 for locking transfer elements of the transfer interface 110. At step S301, the transfer interface 110 is shown before extension of one of the transfer elements. The unextended transfer element may be contained within the containing tube 209. At S303, an extended transfer element 351 is shown extending from the containing tube 209 in order to collect a sample from the disposable container 102.

An operating element or switch may cause the transfer element to extend from the transfer interface. The extended transfer element 351 may extend past (or beyond) the plate 201. During extension, the transfer element may pierce the septum behind the plate 201.

The switch may be activated when pressed by a user. In particular, the switch may be implemented as the button or a toggle switch. At S305, the extended transfer element 351 may retract, e.g., because the switch has been deactivated. When implemented as a button, the switch may be deactivated when the user releases the button. The extended transfer element 351 may retract into the containing tube 209. The transfer element may have a corresponding biasing element and retraction of the extended transfer element 351 may be effected via the biasing element.

The biasing element may be implemented as a spring or as another device capable of exerting a biasing force.

At S305 the locking mechanism 353 locks the transfer element such that the transfer element cannot be extended. Accordingly, even if the switch is activated, the transfer element will not be extended. However, activation of the switch may cause the extension of another transfer element of the transfer interface 110, different from the transfer element that was extended. Retraction of the transfer element may be caused by deactivation of the switch. In particular, deactivation of the switch may cause the extended transfer element 351 to retreat into the body of the transfer interface 110, as shown at S305.

The locking mechanism 353 may be triggered to lock the transfer element upon deactivation of the switch. Deactivation of the switch may be effected by the user releasing the button or when the user engages the switch a second time (e.g., press the button once for activation and a second time for deactivation). Alternatively, the switch may be manually toggled (e.g., similar to a light switch being switched off) in order to effect deactivation of the switch.

The locking mechanism 353 may also be triggered automatically. For example, the extended transfer element 351 may retract after a certain amount of time rather than upon user-triggered deactivation of the switch. The locking mechanism 353 may then be triggered by the retraction of the extended transfer element 351.

The locking mechanism 353 may help ensure that samples can be extracted or collected from the container 102 in a sterile manner, particularly by preventing an transfer element from being used multiple times.

Figure 4:
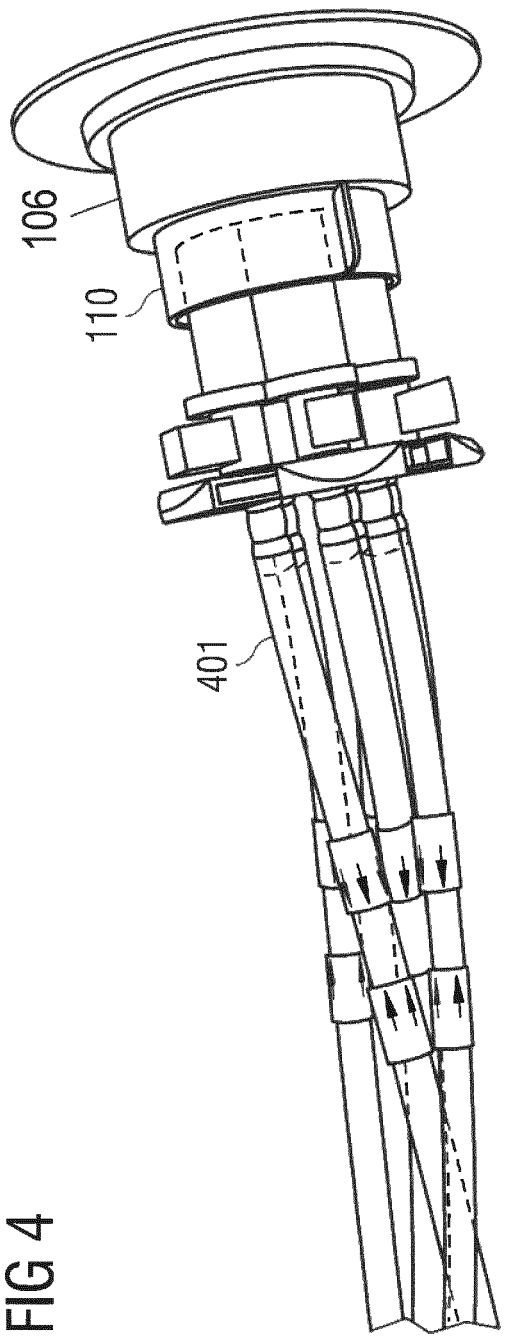
FIG. 4 also shows the transfer interface.

FIG. 4 depicts the transfer interface 110 connected to the port 106.

The distribution tubes 401 extend from the body of the transfer interface 110. The distribution tubes 401 extend in an axial direction. The distribution tubes 401 may carry samples collected from the container 102 via the transfer elements away from the container 102. The samples may be fluid.

Figure 5:
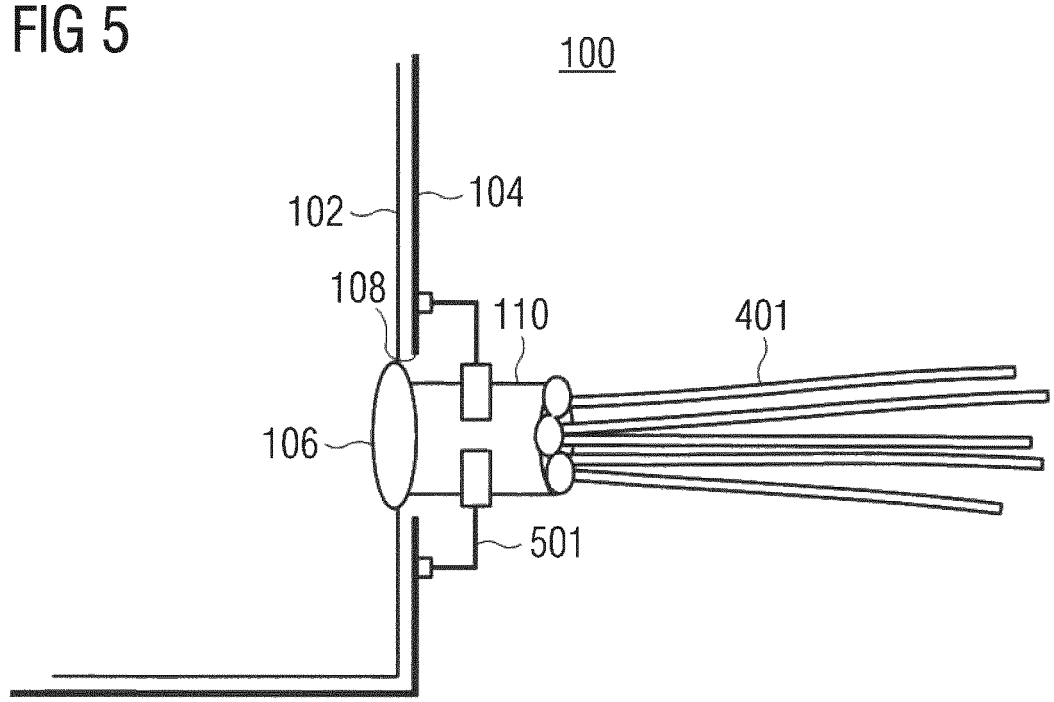
FIG. 5 shows a mounting bracket for supporting the transfer interface when the transfer interface is connected to the port.

FIG. 5 shows a part of the system 100 for transferring chemical, pharmaceutical, or biological material into or out of the container 102. Depicted are a part of the housing 104 supporting the container 102. Also depicted is the port 106. Connected to the port 106 is the transfer interface 110. A mounting bracket 501 may support the transfer interface 110.

The mounting bracket 501 may be attachable to the transfer interface 110. The mounting bracket 501 may fit around a body of the transfer interface 110.

The mounting bracket 501 may be attached to the housing around the opening 108. Further, the mounting bracket 501 may center the transfer interface at the port 106.

Figure 9:
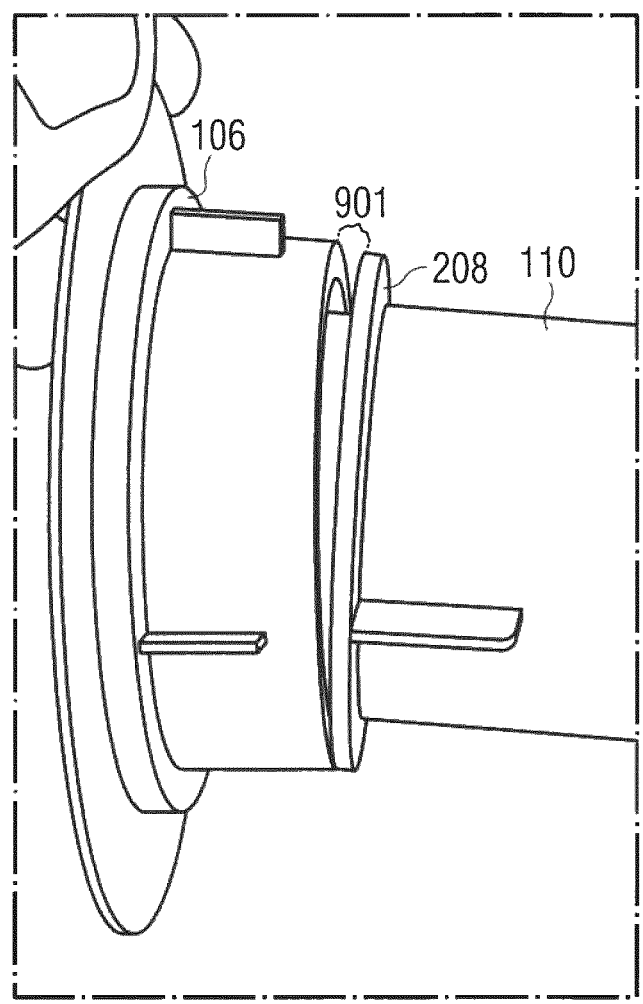
FIG. 9 shows bending of the transfer interface away from the port of the disposable container.

Use of the mounting bracket 501 may prevent the transfer interface 110 from being prematurely detached from or misaligned with the port 106 (as shown in FIG. 9) and may stabilize the transfer interface. Further, the mounting bracket 501 may help keep the plate 201 parallel to the surface of the container 102 and hinder deformation of the transfer interface 110. Accordingly, use of the mounting bracket 501 may help enable extraction of samples from the container while maintaining sterility, such that undesirable elements (e.g., undesired germs or microorganisms) are not introduced into the container 102.

Figure 6:
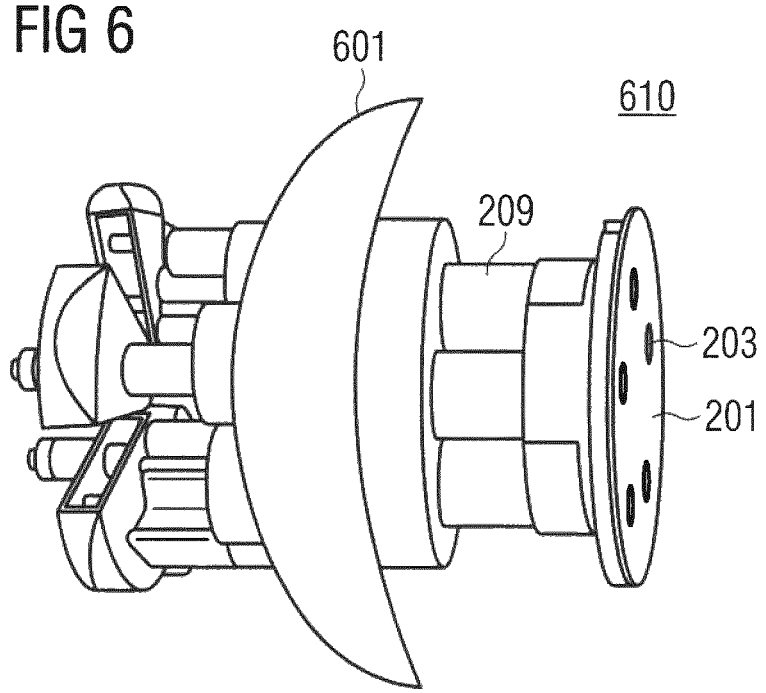
FIG. 6 shows another transfer interface including a crescent shaped grip.

FIG. 6 shows the transfer interface 110. According to the depicted example, the transfer interface 110 includes a grip 601. The grip 601 may have an ergonomic shape enabling easy removal of the transfer interface 110 from the port 106. The grip 601 may also facilitate attaching the transfer interface 110 to the port 106. The grip 601 may have a crescent shape such that tips of the crescent protrude from opposing sides of the transfer interface 110. Other shapes that fulfill the ergonomic function of the grip 601 are also possible. The grip 601 may support the fingers of the user as the transfer interface 110 is attached to or removed from the port 106.

Figure 7:
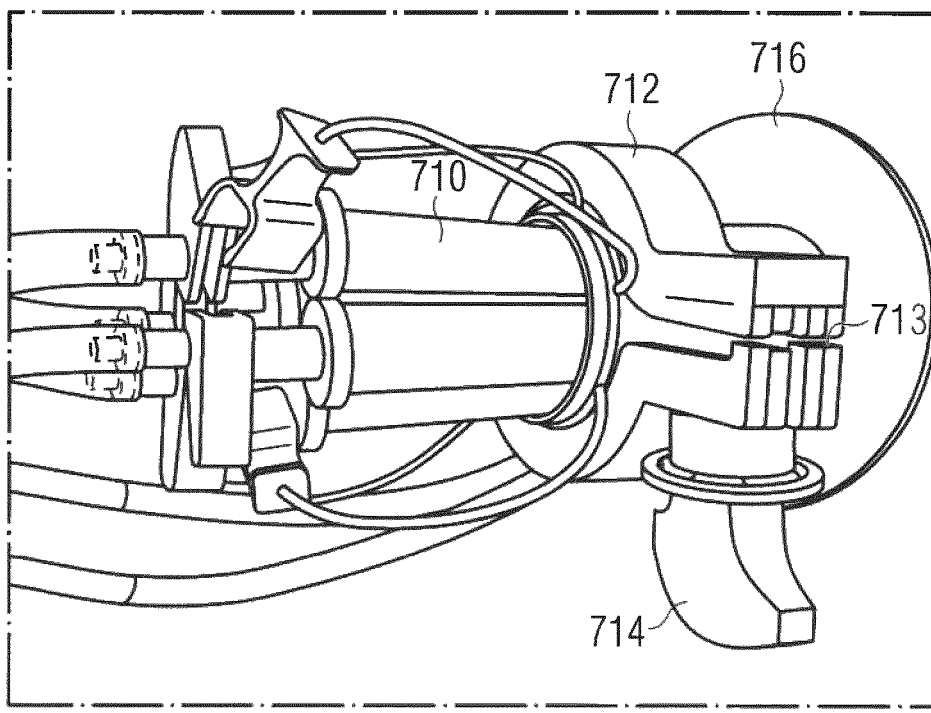
FIG. 7 shows a multi-use transfer interface connected to a container via a triclamp.

FIG. 7 shows a multi-use transfer interface 710 connected to a container. The container may be the container 102 or a different container (e.g., a reusable container). The multi-use transfer interface 710 may be connected using a triclamp 712. Accordingly, the container may include a triclamp port 716. The triclamp 712 may also be referred to as a sanitary clamp.

The multi-use transfer interface 710 may be used to collect samples from or insert substances into the container, as discussed in connection with the transfer interface 110 and the container 102.

The triclamp 712 may include two clamp prongs or members pivotably connected to one another at a hinge 713. The triclamp 712 may include a lock and a fastening element 714. The lock may be referred to as a triclover and can be removable or permanently locked.

Twisting of the fastening element 714 may cause the prongs of the triclamp 712 to close around the transfer interface 710, thereby securing it to the port 716. The triclamp 712 may create a compressing clamping force to join the transfer interface 710 to the port 716. The triclamp 712 may include an elastomeric seal compressed or sandwiched between the two prongs, thereby creating a connection that is air tight and that can withstand elevated pressure conditions. The triclamp 712 may hold the transfer interface 710 in sealed engagement with the port 716.

Advantages of the triclamp 712 (or a similar element) connection as shown in FIG. 7 are that the triclamp 712 is reliable and standardized. In particular, the triclamp 712 (or a similar connection) may be commonly used in equipment (e.g. containers) used to process chemical, pharmaceutical and/or biological material, particularly stainless steel equipment (e.g., vessels, pumps, fluid transfer piping, filtering devices, bioreactors).

The triclamp 712 could also be used in the context of a single-use container, e.g. the container 102. However, the triclamp 712 requires multiple parts. Accordingly, manufacturing and/or assembling the clamp may be complicated. Further, the fastening element 714 may present problems with regard to the sterility of the container 102. In particular, it might be preferable to use a permanent clamp that cannot be unfastened in order to ensure that the container 102 is kept sterile. Also, the triclamp 712 may be bulky and/or heavy and difficult to assemble for a single user or operator The multi-use transfer interface 710 may be used to collect samples from the container. It may be desirable to collect the samples in such a way that they reflect the content of the container as a whole. In other words, the content of the collected samples should be homogenous with the content of the container. For a 1½ (3.81 cm) triclamp size, the classical distance between triclamp connection interface and the container wall (or surface) is greater than 20 mm, which may create dead volume in the port 716. In particular, it may be desirable to reduce the distance between a transfer interface (e.g., the transfer interface 710) and a surface (or wall) of the container (e.g., the container 102) to less than 20 mm, more specifically, less than 10 mm or less than 5 mm.

Accordingly, it may be difficult to connect the transfer interface 110 to the disposable container 102 such that the transfer interface 110 is parallel to a wall or surface of the disposable container 102.

Moreover, it may be difficult to connect the transfer interface 110 to the disposable container 102 such that the plate 201 at least partly contacts the surface of the container and there is less than a specified distance between the plate 201 and the surface of the container. In particular, the specified distance between the surface (i.e. exterior surface, outer surface or wall) of the disposable container 102 and the transfer interface 110 connected to the port 106 may be one to five millimeters. Accordingly, it may be desirable that the plate 201 is substantially flush with the surface of the container 102, such that no part of the plate 201 is more than five millimeters from surface of the container 102 when the transfer interface 110 is connected to the port 106.

As noted above, it may be desirable that all samples extracted from the container 102 be representative of the entire contents of the container 102, i.e., all samples are homogeneous. Maintaining a minimum distance (i.e., the specified distance) between the transfer interface 110 and the container 102 may help ensure that a sample extracted from the container 102 is homogenous with the contents of the container 102. If the transfer interface 110 is not substantially flush with the surface (e.g., a wall) of the container 102, e.g., the distance between an end of the transfer interface 110 and the wall of the container 102 is greater than the specified distance, this may result in extraction of a sample that differs from the contents of the container 102 as a whole. In particular, more than the specified distance between the transfer interface and the wall of the container 102 may result in extraction of heterogeneous samples. Such heterogeneous samples may not have the same properties as the contents of the container 102 as a whole, which may limit their usefulness.

Figure 8:
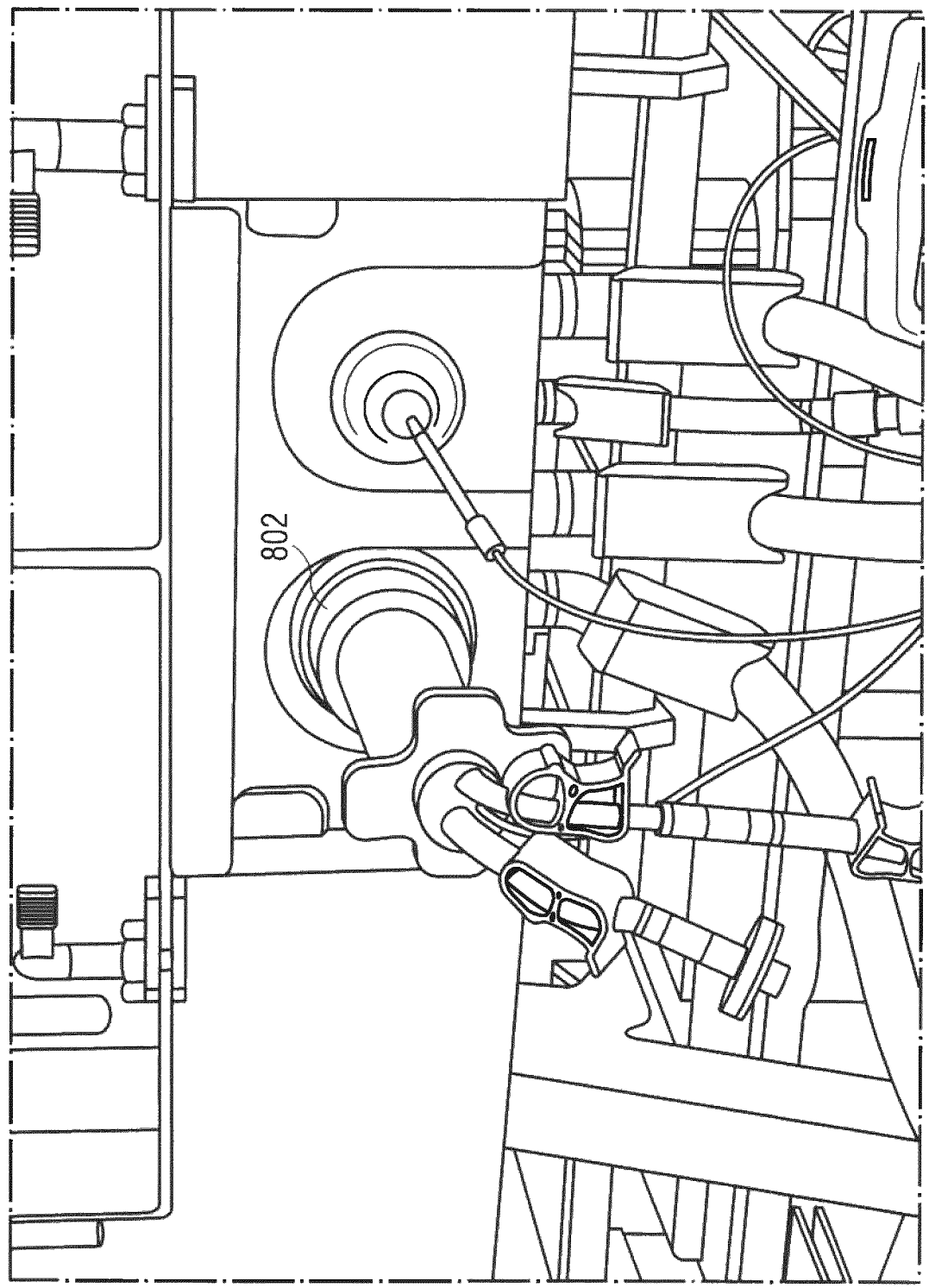
FIG. 8 shows the single-use container including multiple ports and interfaces.

FIG. 8 shows the container 102. In the example of FIG. 8, a sensor port 802 is used for a pH sensor connection. The sensor port 802 may be an implementation of the port 106.

FIG. 9 shows a problem that may arise when using the transfer interface 110. In particular, a compromised connection between the transfer interface 110 and the port 106 is shown. In this case, the transfer interface 110 has been connected to the port 106, but the plate 201 is no longer parallel to the surface of the container 102.

The compromised connection may result in deformation of the port 106 and/or the transfer interface 110. In the case of the compromised connection, at least part of the stopping flange 208 might no longer contact the port 106. Such a compromised connection may result in leakage from the container 102 and/or loss of sterility.

The problem shown in FIG. 9 may arise for one or more of the following reasons.

In particular, the port 106 may be made of flexible or bendable material. For example, the port 106 may be made from thermoplastics welded onto the container 102 (e.g., polyethylene) rather than a more rigid substance, such as rigid plastic (e.g., rigid PVC) or metal.

Further, the length and/or the weight of the transfer interface 110 may be substantially greater than the length of the port 106 which extends from the container 102. Moreover, extraction of samples from the container 102 may put stress on the connection between the port 106 and the transfer interface 110. Accordingly, the port 106 may be deformed, such that there is a gap 901 between the stopping flange 208 and the port 106, as shown. The gap 901 between the stopping flange 208 and the port 106 may be created due to the weight of the transfer interface 110 and/or use of the transfer interface 110. The gap 901 between the stopping flange 208 and the port 106 may form even after the transfer interface 110 has been permanently connected to the port 106, e.g., via the bayonet connection, triclamp connection with non-removable triclover, another kind of permanent mechanical connection and/or an adhesive such as glue. However, even the permanent connection may not be sufficient to prevent the gap 901 from forming.

When the gap 901 is present, the plate 201 is not parallel to the surface of the container 102.

Figure 10:
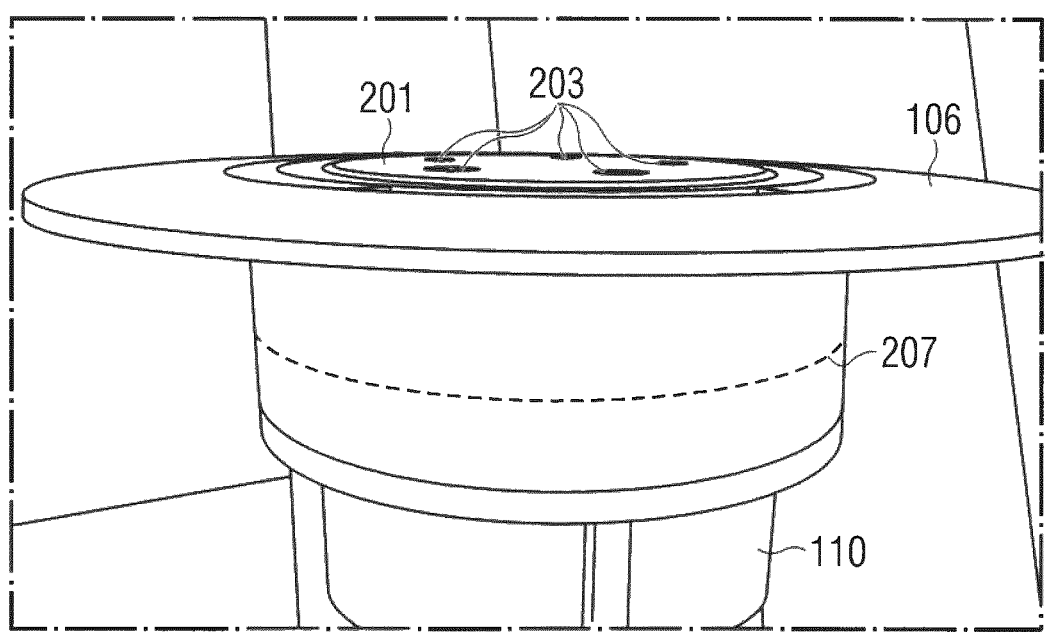
FIG. 10 shows the transfer interface connected to the disposable container in which the plate is parallel to a surface of the container.

FIG. 10 shows the transfer interface 110 connected to the port 106. The O-ring 207 of the transfer interface 110 is visible through the port 106.

When connected to the port 106, the plate 201 may be aligned with a flange of the port 106 (e.g., the plate 201 may be aligned with the port flange 1203). The plate may be parallel to an interior part of the port 106. Accordingly, the plate 201 may be substantially flush with the surface (i.e., wall) of the container 102. Alternatively, the plate 201 may be opposite an opening in the surface of the container 102 and substantially parallel to a portion of the surface surrounding the opening.

In order to effect connection of the transfer interface 110 to the port 106, the bayonet connection may be used. In particular, the transfer interface 110 may be pushed into the port 106 such that at least a portion of the transfer interface 110 is contained within the port. The transfer interface 110 is then arranged so that the connecting flange 204 is under the respective connecting protrusion 1201. The arranging may be effected by twisting the transfer interface 110 in order to lock the transfer interface 110 in place.

The plate 201 may contact (e.g., the plate 201 may be substantially flush with) the surface of the container 102. Accordingly, when connected, the plate 201 may be substantially flush with the surface of the flexible wall of the container 102. In particular, there may be no more than the specified distance between the wall of the container 102 and the plate 201. Further, it is possible that the plate 201 is slightly convex, so as to effect a tighter connection between the transfer interface 110 and the container 102. Thus, when pushed together there may be a plurality of points of contact (e.g., many) between the plate 201 and the surface of the container 102, such that no more than the specified distance exists between any point on the plate 201 and the surface of the container 102. It is also possible that the surface of the container 201 is elastic, e.g. compressible silicone, such that it resists a distorting influence or deforming force and returns to its original shape when the force is removed.

Further, a surface of the container 102 accessible through the port 106 (i.e., opposite the port 106) may differ from the rest of the surface of the container 102. For example, the surface accessible through the port 106 may be more flexible or compressible than the rest of the container 102.

Rather than being in contact with the surface of the container 102, the plate 201 may be opposite an opening in the container 102. In this case, if the surface of the container 201 were contiguous (i.e., the opening did not exist), the plate 201 would contact the surface of the container 201 when the transfer interface 110 is connected to the port 106. Thus, when the transfer interface 110 is connected, the plate 201 may be substantially level with the surface of the container surrounding the opening.

In either case (i.e., with or without an opening in the container 201), the plate 201 may be parallel to the surface of the container 201.

The O-ring 207 may be colored such that it is visible when the transfer interface 110 is connected to the port 106, as shown in FIG. 10. The O-ring 207 may be used to ensure that the transfer interface 110 is connected to the port 106 and that the transfer interface 110 is in the correct position.

Figure 11:
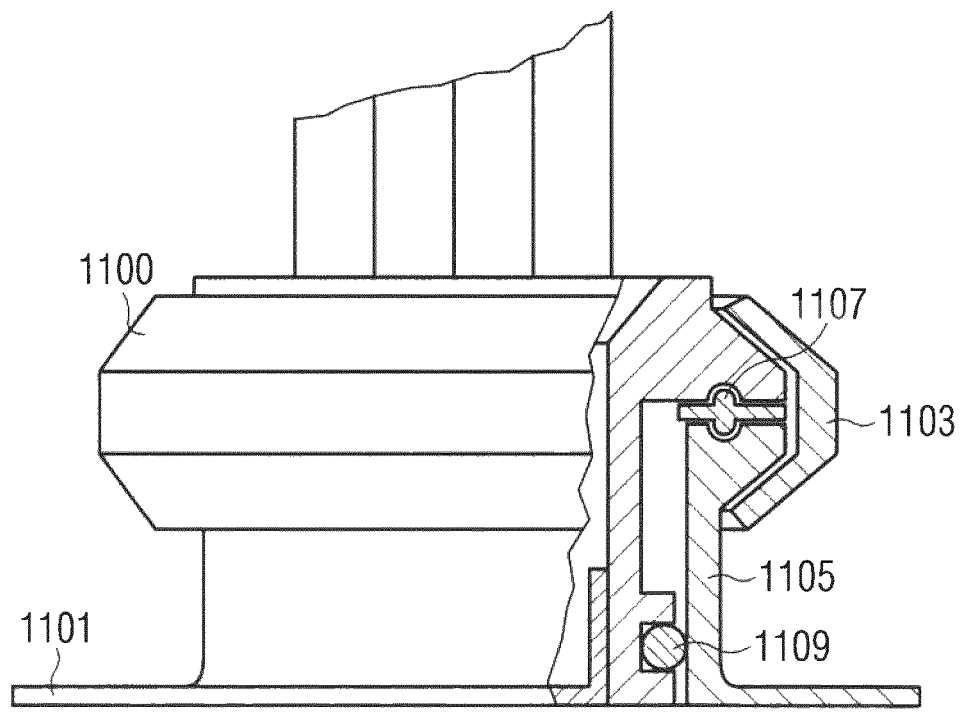
FIG. 11 shows a modified triclamp connection used to connect a transfer interface to the disposable container.

FIG. 11 shows an example of a transfer interface 1100 connected to a port 1101 using a triclamp 1103. The triclamp 1103 may be similar or identical to the clamp 712 described in the context of FIG. 7. Further, the port 1101 may be similar to the port 716 described in the context of FIG. 7. The port 1101 may differ from the port 716 in that the port 1101 is connected to the container 102. The transfer interface 1100 may be similar or identical to the transfer interface 710. The transfer interface 1100 may include the plate 201 (not shown).

The cut-out visible in FIG. 11 may show a cross-section of the transfer interface 1100 and the port 1101. The port 1101 may differ from the port 716 in that the port 1101 includes a supporting protrusion 1105 that extends substantially further from the container 102 than any part of the port 716. In other words, the supporting protrusion 1105 may extend further from the container 102 than any comparable extension of the port 716 extends from the container discussed in connection with FIG. 7. For example, the supporting protrusion 1105 may extend about 40-60% further, preferably about 50% further from the container 102 than the port 716 extends from the container described in the context of FIG. 7.

The supporting protrusion 1105 may provide additional support or guidance for the transfer interface 1100, particularly in view of its additional length (i.e., the additional distance that the supporting protrusion 1105 extends from the container 102 in comparison to the distance that the port 716 extends from the container described in the context of FIG. 7). This may prevent the connection between the transfer interface 1100 and the port 1101 from being compromised, e.g. as shown in FIG. 9. Thus, the supporting protrusion 1105 may keep the plate 201 of the transfer interface 1100 at least partly in contact with the surface of the container 102 when the transfer interface 1100 is connected to the port 1101. In some cases, the supporting protrusion 1105 may keep the plate 201 parallel to (e.g., substantially flush with) the surface of the container 102 when the transfer interface is connected to the port 1101.

In particular, the design shown in FIG. 11 may prevent a gap from forming between the transfer interface 1100 and the port 1101 such that the plate 201 is no longer parallel to the surface of the container, as discussed in connection with FIG. 9. A clamp gasket 1107 may facilitate provision of an air tight connection between the transfer interface 1100 and the port 1101. Further, an O-ring 1109 may also facilitate an air tight connection between the transfer interface 1100 and the port 1101.

Accordingly, the configuration shown in FIG. 11 may limit potential deformation of parts of the transfer interface 1100. In particular, there may be a risk of such deformation when parts of the transfer interface 1100 are formed from a flexible material, e.g., flexible plastic.

The configuration shown in FIG. 11 may prevent the deformation or disconnection of the transfer interface 1100, as shown in FIG. 9.

FIG. 12A shows another transfer interface 1210 and the port 106. Unless otherwise indicated, the transfer interface 1210 corresponds to the transfer interface 110. Specific parts of the transfer interface 1210 that correspond to (e.g., are the same as) parts of the transfer interface 1210 are given the same reference signs.

In FIG. 12A, the port 106 includes a connecting protrusion 1201 extending parallel to the container 102. FIG. 12A shows a cross-section of the connection between the transfer interface 1210 and the port 106. The connecting protrusion 1201 may extend radially inward from the stopping protrusion 1205.

In addition, the port 106 includes a port flange 1203. The configuration of FIG. 12 may be used to ensure that the plate 201 of the interface 1210 is parallel to the surface of the disposable container 102 (not shown). For example, the transfer interface 1210 may be connected to the port 106 by arranging the connecting flange 204 under the connecting protrusion 1201 such that the plate 201 contacts the surface of the container 102. Alternatively, the plate 201 may be aligned with an opening of the container 102 when the transfer interface 1210 is connected to the port 106.

The plate 201 may be a relatively inflexible material (e.g. metal, such as aluminum) and the surface of the container 102 may be a flexible material (e.g., a flexible plastic such as flexible PVC). In particular, when the connecting flange 204 is underneath the connecting protrusion 1201 the surface of the container 102 may exert a biasing force on the plate 201. In other words, the surface of the container 102 pushes against the plate 201.

Similar to the transfer interface 110, the transfer interface 1210 includes a connecting flange 204 extending from the plate 201. There may be two diametrically opposed connecting flanges 204, e.g., as shown in FIG. 2.

Accordingly, to effect connection of the transfer interface 1210 to the port 106, the transfer interface 1210 may be pushed into the port 106. For example, the transfer interface 1210 may be pushed against the surface of the container 102 such that the plate 201 is substantially flush with the surface of the container. The transfer interface 1210 may then be twisted so that the connecting flange 204 is arranged under the connecting protrusion 1201. This arrangement may cause the plate 201 to contact the surface of the container 102, or may cause the plate 201 to cover the opening in the surface of the container 102 accessible through the port 106. In particular, the plate 201 may be kept parallel to the surface of the container via the arrangement of the connecting flange 204 under the connecting protrusion 1201.

Arranging the connecting flange 204 under the connecting protrusion 1201 may involve pushing the transfer interface 1210 against the surface of the container 102.

The arrangement of the connecting flange 204 under the connecting protrusion 1201 may ensure that a pressing force is applied against the surface of the container 102 by the plate 201 so as to keep the plate 201 substantially flush with the surface of the container 102.

Further, the plate 201 may be adapted to conform to the surface of the container 102. For example, the plate may be slightly convex so as to exert a greater pressing force on the surface of the container 102. The surface of the container accessible through the port 106 may be different from the rest of the surface of the container 102. In particular, the surface of the container 102 accessible through the port 106 may be silicone whereas the surface of the rest of the container 102 may be nylon or polyethylene. Alternatively, the entire surface of the container 102 may be made of silicone or a flexible plastic material.

It may be sufficient that the plate at least partly contacts the surface of the container 102. In particular, it may be sufficient if there is no more than the specified distance separating portions of the plate 201 from the surface of the container 102. Alternatively, the entire plate may be in contact with the surface of the container 102. In some cases, it may also be desirable to reduce the distance between any portion of the plate 201 and the surface of the container 102 to a distance of less than the specified distance, i.e., such that the plate 201 is substantially flush with the port 106.

As noted above, the specified distance may be one to five millimeters. In particular, the specified distance may be three millimeters.

The O-ring 207 and the internal flanges 205 may help ensure that there is a seal between the transfer interface and the container 102 and that any extracted sample from the container is homogeneous with the entire content of the container 102.

The configuration of FIG. 12A may also help prevent the connection between the transfer interface 1210 and the port 106 from being compromised, e.g., due to the weight of the transfer interface and/or usage of the transfer interface 1210.

In particular, the transfer interface 1210 may include a stopping flange 1208 that differs from the stopping flange 208.

Figure 12B:
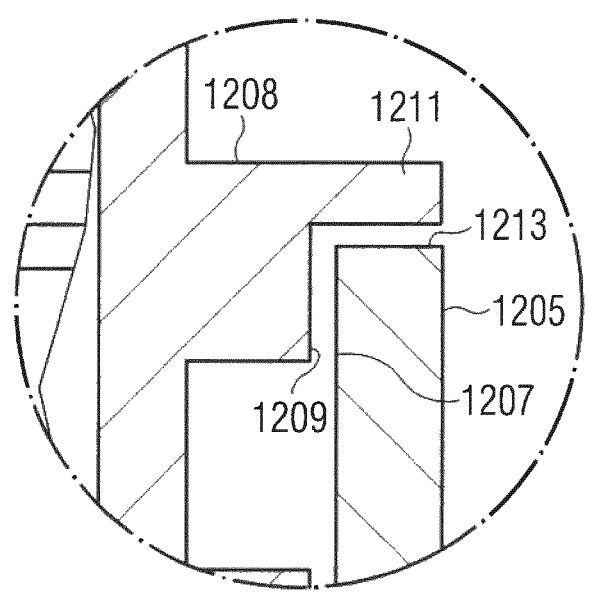
FIG. 12B shows part of the connection of FIG. 12A in more detail.

As shown in more detail in FIG. 12B, the stopping flange 1208 may include a flat portion 1209 and an extending portion 1211. Further, the port 106 may also comprise a stopping protrusion 1205.

When the transfer interface 1210 is connected to the port 106, the stopping protrusion 1205 may contact the stopping flange 1208. More specifically, the stopping protrusion 1205 may include an extending part 1207 that contacts the flat portion 1209 of the stopping flange 1208.

The extending portion 1211 of the stopping flange 1208 may contact a parallel part 1213 of the stopping protrusion 1205. Accordingly, the extending part 1207 of the stopping protrusion 1205 may extend away from the container 102. The parallel part 1213 of the stopping protrusion 1205 may extend in a direction substantially parallel to the surface of the container 102. The parallel part 1213 may be substantially parallel to the connecting protrusion 1201 and the extending portion 1211.

Accordingly, when the transfer interface 1210 is connected to the port 106, the contact between the stopping flange 1208 and the stopping protrusion 1205 may prevent the connection between the transfer interface 1210 and the port 106 from being compromised, especially because of the weight of the transfer interface 1210 and/or use of the transfer interface 1210. In particular, the step-configuration of the stopping flange 1208, shown in FIGS. 12A and 12B, may provide further support to the rest of the transfer interface 1210 in comparison to the configuration of the transfer interface 110, thereby preventing the compromised connection shown in FIG. 9. Deformation of the transfer interface 1210 and/or the port 106 may also be prevented.

More particularly, when the transfer interface 1210 is connected to the port 106, the extending portion 1211 may contact the parallel part 1213, as shown in FIG. 12B. Simultaneously, the flat portion 1209 may contact the extending part 1207. The combination of the flat portion 1209 and the extending portion 1211 may form a step. Upon connection of the transfer interface 1210, the step may interact with or engage with the extending part 1207 and the parallel part 1213. The engagement may provide increased stability of the transfer interface 1210 and prevent deformation of the transfer interface 1210, e.g., as shown in FIG. 9.

When the transfer interface 1210 is connected to the port 106, the extending portion 1211 abuts the parallel part 1213 of the stopping protrusion 1205. Further, the flat portion 1209 abuts the extending part 1207 of the stopping protrusion 1205. The abutment or contact makes it possible for the stopping protrusion 1205 to provide further support for the transfer interface 1210.

The stopping protrusion 1205 may be substantially cylindrical. In particular, the stopping protrusion 1205 may form a hollow elliptic or circular cylinder. The connecting protrusion 1201 may extend radially inward from the stopping protrusion 1205.

The connecting protrusion 1201 may cover only a part of the inner circumference of the stopping protrusion 1205. For example, a quarter of the inner circumference of the stopping protrusion 1205 may be covered by the connecting protrusion 1201. A second quarter of the stopping protrusion 1205 may be covered by a gap, followed by another portion of the stopping protrusion 1201 followed by another gap. Accordingly, about half of the circumference of the stopping protrusion 1205 may be covered by the connecting protrusion 1201.

In the context of the present application, the term "circumference" does not necessarily imply a circular shape. For example, the shape could be elliptical or substantially circular.

Similar to the stopping flange 1208 with respect to the transfer interface 110, the stopping flange 1208 may extend radially outward from the transfer interface 1210. The stopping flange 1208 may cover the entire circumference of the transfer interface 1210. In other words, the stopping flange 1208 may extend radially outward along the entire circumference of the transfer interface 1210.

The at least one connecting flange 204 may extend radially outward from the plate 201. At least part of a circumference of the plate might not be covered by the connecting flange 204. In other words, the connecting flange 204 might not extend outward from portions of the plate 201. The pattern of portions of the connecting protrusion 1201 and gaps along the stopping protrusion 1205 may mirror the connecting flange 204 and gaps between the connecting flange 204 along the circumference of the plate 201. In particular, the may be two diametrically opposed connecting flanges 204 mirrored by two connecting protrusions 1201.

Accordingly, substantially half of the circumference of the transfer interface may be covered by the at least one connecting flange 204. In other words, the connecting flange 204 may extend radially outward from about half of the circumference of the transfer interface 1210. Along the other half of the circumference of the transfer interface 1210 there may be gaps between the at least one connecting flange 204.

The connecting flange 204 may extend radially outward from the transfer interface at the location of the plate 201. The connecting flange 204 may be in contact with the surface of the container 102 when the transfer interface 1210 is connected to the port 106. Alternatively, the connecting flange 205 may hold the plate 201 over an opening in the surface of the container 102, such that the plate 201 is substantially level with a portion of the surface surrounding the opening. The transfer interface 1210 may be permanently connected to the port 106, e.g., through use of an adhesive. The permanent connection between the transfer interface 1210 and the port 106 may help ensure stability.

The O-ring 207 may be located between the connecting flange 204 and the stopping flange 1208. More particularly, the O-ring 207 may be located between two internal flanges 205. The two internal flanges 205 may be located between the stopping flange 1208 and the connecting flange 204. Each internal flange 205 may extend radially outward from the transfer interface 1210. Each internal flange 205 may cover the entire circumference of the transfer interface 1210 or approximately the entire circumference of the transfer interface 1210. For example, each internal flange 205 may cover enough of the circumference of the transfer interface 1210 in order to support the O-ring 207. The O-ring 207 may be located between the two internal flanges 205.

The port flange 1203 may extend radially outward from the port 106. The port flange 1203 may help provide stability and help ensure that the plate 201 remains parallel to the surface of the container 102. In addition, along with the step configuration discussed above, the port flange 1203 may help ensure that the connection between the transfer interface 1210 and the port 106 is not compromised, and that the transfer interface 1210 is not deformed through use or via its own weight or via the weight of samples extracted from the container 102.

The O-ring 207 may be colored such that the O-ring 207 is visible from outside the transfer interface 1210. Coloring of the O-ring may facilitate correct insertion of the transfer interface 1210 into the port 106. In particular, if the colored O-ring 207 appears to be straight and symmetrical when the transfer interface 1210 is inserted into the port 106, then it may be assumed that the transfer interface 1210 has been inserted correctly. If the O-ring 207 is visibly crooked or not symmetrical, then it may be assumed that the transfer interface 1210 has not been correctly inserted into the port 106.

The connecting flange 204 and the connecting protrusion 1201 may be parts of the bayonet connection used to connect the transfer interface 1210 to the port 106.

The stopping protrusion 1205 may stop further progress of the transfer interface 1210 toward the container 102. In addition, the stopping protrusion 1205 may impart stability to the transfer interface 1210 and may help prevent the deformation of the transfer interface 1210 shown in FIG. 9. In particular, the combination of the extending portion 1211 and the flat portion 1209 of the stopping flange 1208 as well as the extending part 1207 and the parallel part 1213 of the stopping protrusion 1205 may help prevent the compromised connection and deformation of the transfer interface 1210 discussed above.

There may be a plurality of connecting flanges 204. In particular, there may be two connecting flanges 204. The two connecting flanges 204 may be separated by a first gap and a second gap. Each of the two connecting flanges 204 may extend around approximately a quarter of the circumference of the plate 201. The two portions may be diametrically opposed. Each of the two gaps may also extend around approximately a quarter of the circumference of the plate. The two gaps may be diametrically opposed.

The transfer interface 1210 and the configuration of FIGS. 12A and 12B may have advantages in comparison to the configuration of FIG. 11. In particular, in comparison to the configuration of FIG. 11, the port 106 and the stopping protrusion 1205 might not protrude as far from the container 102 as the supporting protrusion 1105. In particular, the port 106 may be a standard bioreactor port, while the port 1101 might extend substantially further (e.g., 1-3 cm further) from the surface of the container than the port 106. Accordingly, the port 106 may be advantageous in comparison to the port 106 because it may be desirable to keep the container as compact as possible.

Thus, via the stopping protrusion 1205 and the stopping flange 1280, it may be possible to provide a way to prevent deformation of the transfer interface (e.g., the transfer interface 1100 or the transfer interface 110) without including a port on the container 102 that extends any further from the container 102 than the port 106 (e.g., a standard bioreactor port). In particular, it may be desirable to provide the port 106 such that the distance which the port 106 extends from the container 102 is minimized.

The transfer interface 1210 might also be advantageous because of its relatively low weight and simplicity. In particular, the triclamp 1103 may have at least four parts including the gasket 1107, a fastening element similar to the fastening element 714, and two prongs to encompass the transfer element 1100 and the supporting protrusion 1105. Accordingly, while the triclamp 1103 may limit potential deformation of the transfer interface 1100 and keep the transfer interface 1100 substantially flush with the surface of the container, particularly in view of the extended port 1101, the transfer interface 1210 in combination with the port 106 may be even more advantageous because the transfer interface 1210 is a single piece and potential deformation (e.g., resulting from repeated use) can be hindered without a non-standard port extending further than usual from the container 102 (as discussed in the context of FIG. 11).

Figure 13:
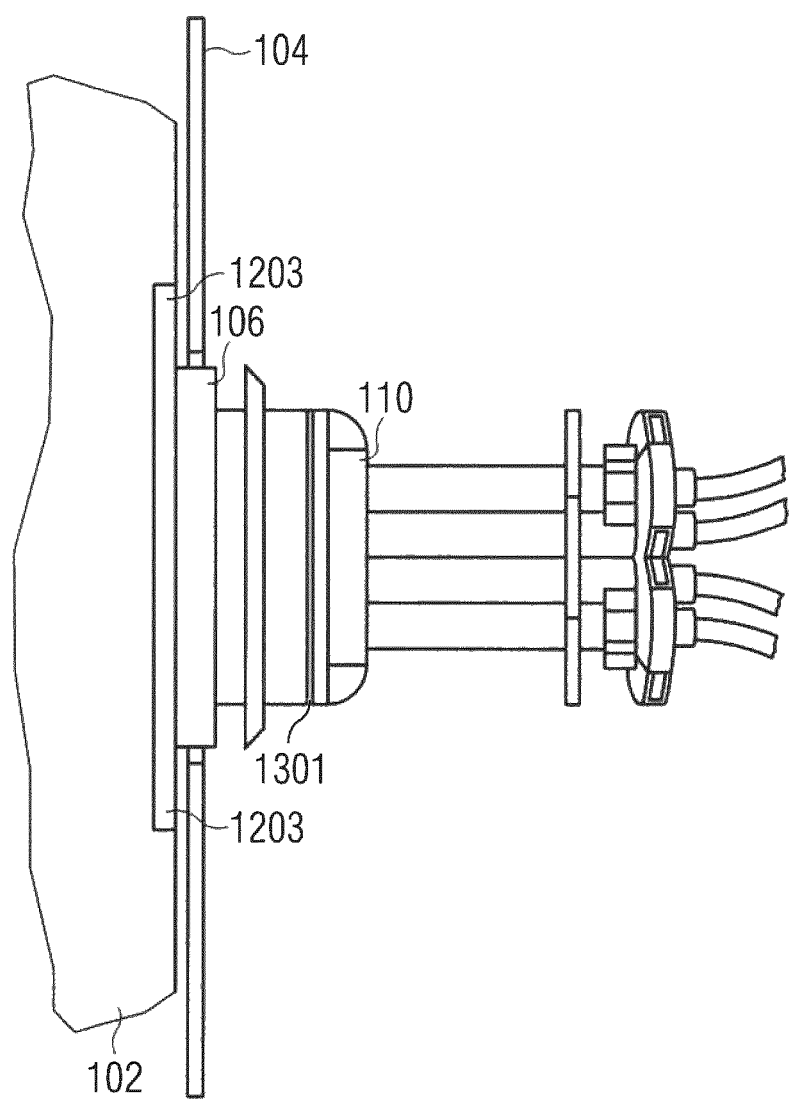
FIG. 13 shows the transfer interface assembled on the port of the disposable container.

FIG. 13 shows the transfer interface 110 connected to the port 106. Unless otherwise indicated, discussion of the transfer interface 110 also applies to the transfer interface 1210.

When connected, the transfer interface 110 is parallel to (e.g., substantially flush with) the surface of the container 102. Port flanges 1203 are shown inside the housing 104. As discussed above, the port flanges 1203 may stabilize the port and the transfer interface 1210. There may be multiple port flanges 1203 or just one port flange 1203. The transfer interface 110 may contact the port 106 at a junction 1301.

The weight of the transfer interface 110 may exert pressure on the port 106, particularly at the junction 1301.

In some cases the weight of the transfer interface 110 may be sufficient to compromise the connection between the transfer interface 110 and the port 106, particularly as shown in FIG. 9. In addition, repeated use of the transfer interface 110 may also cause stress on the port 106 at the junction 1301, possibly in combination with the weight of the transfer interface 110. The effects of the weight of the transfer interface 110 and repeated use of the transfer interface 110 may be mitigated via the step-like connection between the stopping protrusion 1205 and the stopping flange 1208 of the transfer interface 1210, as shown in FIG. 12B.

In addition or alternatively, another approach may be used to prevent deformation of the transfer interface 110 as discussed above and as shown in FIG. 9. This approach, discussed in connection with FIGS. 14-18 below, may also be applied to the transfer interface 1210, in order to decrease the possibility of the compromised connection even further.

Figure 14:
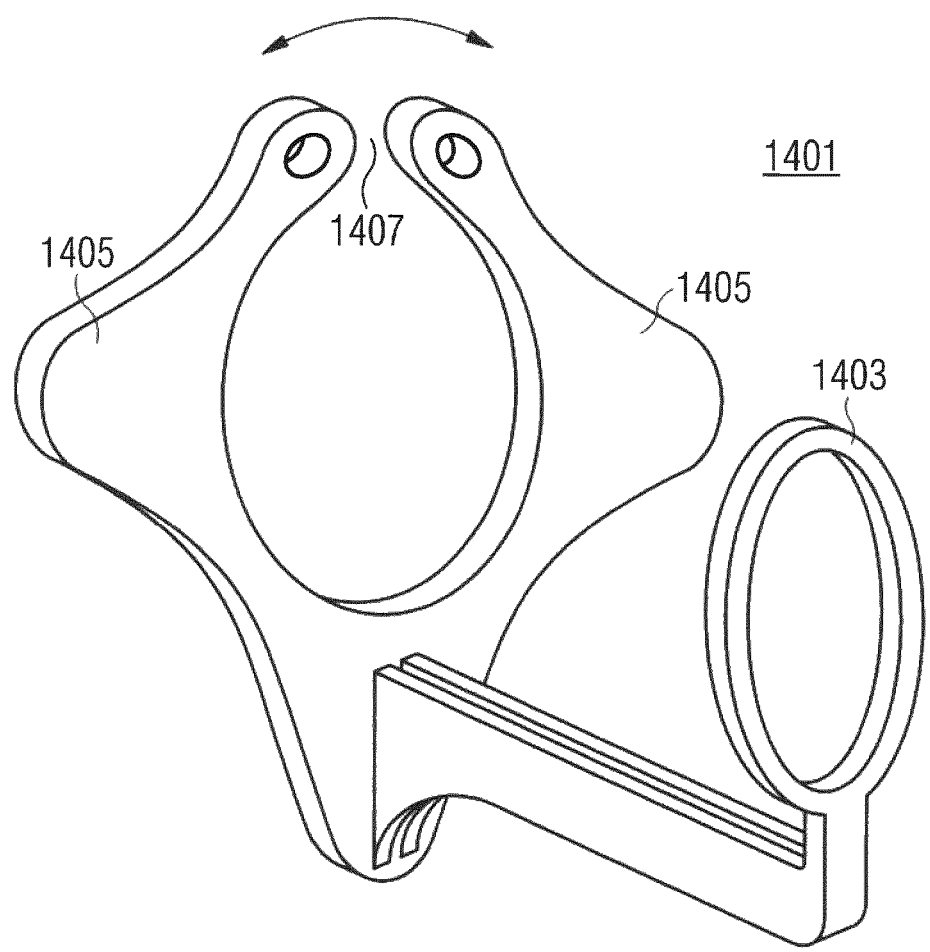
FIG. 14 shows a holder for the transfer interface.

FIG. 14 shows a holder 1401. The holder 1401 may be used to prevent deformation or bending of the transfer interface 110. Although the holder 1401 is discussed in the context of the transfer interface 110 in FIGS. 14-18, the discussion also applies to the transfer interface 1210.

The holder 1401 may support the transfer interface 110 when the transfer interface 110 is connected to the port 106. Accordingly, the holder 1401 may prevent deformation of the transfer interface 110. In addition, the holder 1401 may prevent damage to the container 102. In particular, when the connection between the transfer interface 110 and the port 106 is compromised or the transfer interface 110 is deformed, compression or pressure may be brought to bear on the surface of the container 102, thereby damaging the surface of the container 102.

The holder 1401 may be attachable to the transfer interface 110 and/or the port 106.

For example, the holder 1401 may include an attachment 1403 for the transfer interface 110. The attachment 1403 may have the shape of a ring, as shown in FIG. 14. Other shapes are also possible, as discussed below.

The holder 1401 may also include lateral extensions 1405. The lateral extensions 1405 may contact the housing 104 or the surface of the container 102 when the transfer interface 110 is connected to the port 106. The lateral extensions 1405 may be referred to as wings or supporting elements. The lateral extensions 1405 may support the transfer interface via the attachment 1403. In particular, the lateral extensions 1405 may help distribute the weight of the transfer interface 110 across the surface of the container 102.

The arrows shown in FIG. 14 indicate that the holder 1401 can easily be twisted around the longitudinal axis of the transfer interface 110 until it is placed in the appropriate location. Further, the holder 1401 may be installed after the transfer interface has been permanently fixed to the port 106, but before the distribution tubes 401 are put in place.

The holder 1401 may be plastic or metal. The holder 1401 can be designed with or without the lateral protrusions 1405. The design of the lateral protrusions 1405 may be adapted to the container 102. For example, different lateral protrusions 1405 may be used depending on whether the container 102 is within the housing 104 and the lateral protrusions 1405 will rest against the housing 104 or the container 102 is without the housing 104.

In addition, if the housing 104 is not present, the shape of the lateral protrusions 1405 may differ depending on the flexibility or rigidity of the surface of the container 102.

The installation of the holder 1401 onto the transfer interface 110 may be quick and easy. In particular, the holder 1401 may be attached or clipped to the transfer interface 110 and the port 106 after the transfer interface 110 has been connected to the port 106. Accordingly, the holder 1401 may be attached at virtually any point of the transfer interface rotated until an opening 1407 is vertically aligned with a vertical plane of the container 102 (i.e., the vertical plane of the contents of the container 102) and then slid along the longitudinal axis of the transfer interface 110 toward the surface of the container 102 until being fitted into place, as discussed in the context of FIGS. 16 and 17.

Figure 15:
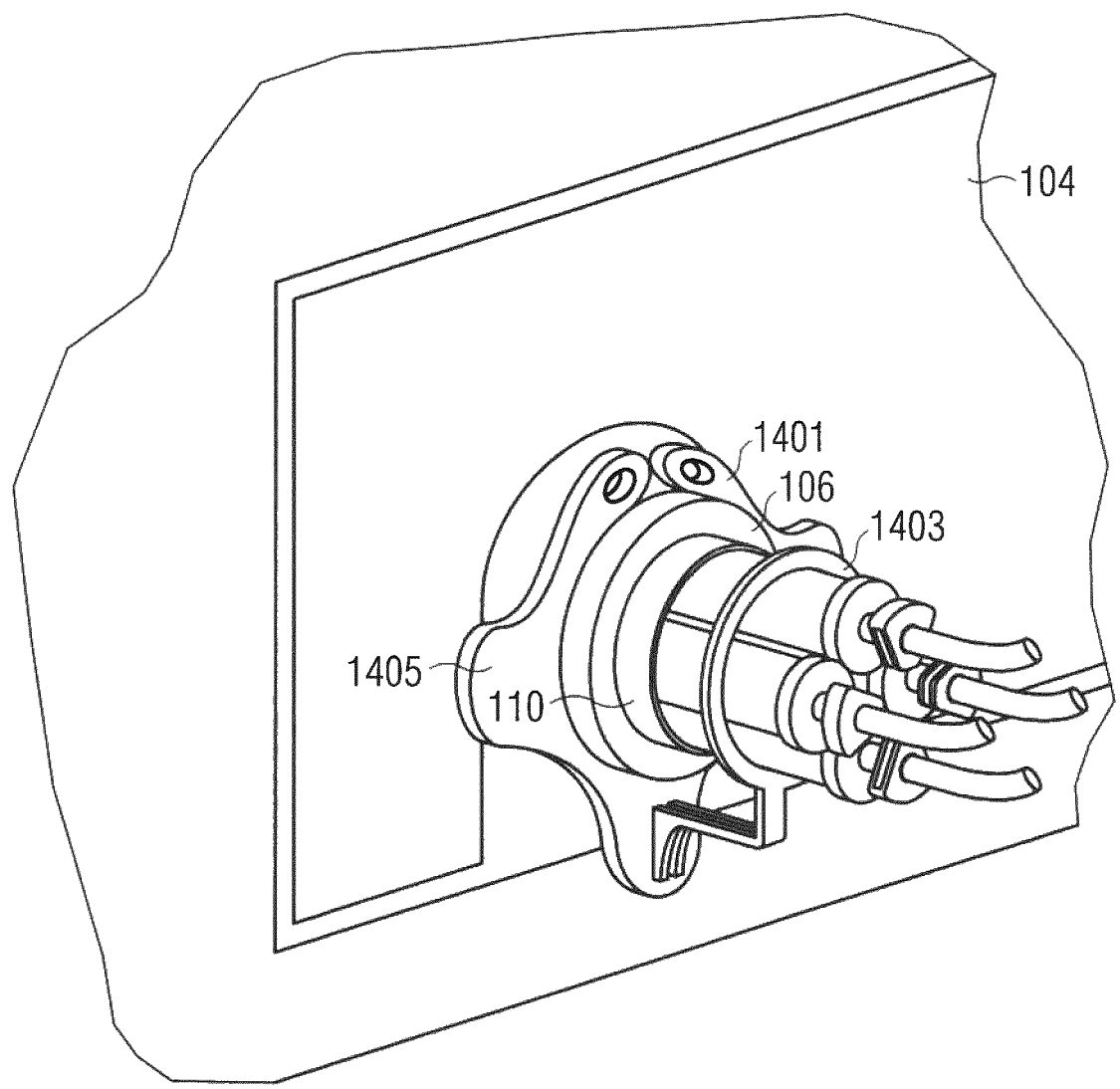
FIG. 15 shows the holder used to connect the transfer interface to the disposable container.

FIG. 15 shows the transfer interface 110 attached to the port 106 using the holder 1401. The attachment 1403 supports the transfer interface 110. The lateral extensions 1405 distribute the weight of the transfer interface 110 across the housing 104. In particular, by use of the lateral extensions 1405, weight of the transfer interface 110 may be distributed across the housing 104 rather than the surface of the container 102. The housing 104 may be better able to absorb the weight of the transfer interface 110 than the surface of the container 102. In particular, the housing 104 may be made of a relatively rigid plastic (e.g., rigid thermoplastic such as nylon) or metal.

The holder 1401 may be used in combination with the transfer interface 110 or with the transfer interface 1210 discussed in connection with FIGS. 12A and 12B. In particular, the holder 1401 may be sufficient to prevent deformation of the transfer interface 110 or damage to the surface of the container 102.

It should be noted that the lateral extensions 1405 are optional. In other words, the holder 1401 may be used without the lateral extensions 1405. In particular, while the lateral extensions 1405 may help distribute the weight of the transfer interface 110 across the housing 104, the holder 1401 may be sufficient to support the transfer interface 110 without the lateral extensions 1405.

The lateral extensions may be positioned against the housing 104, as shown in FIG. 15. Alternatively, the lateral extensions may be positioned directly against the surface of the container 102. The lateral extensions 1405 may help to distribute the weight of the transfer interface 110 across the surface of the container 102, e.g., in order to reduce the amount of force concentrated in one particular area.

Figure 16:
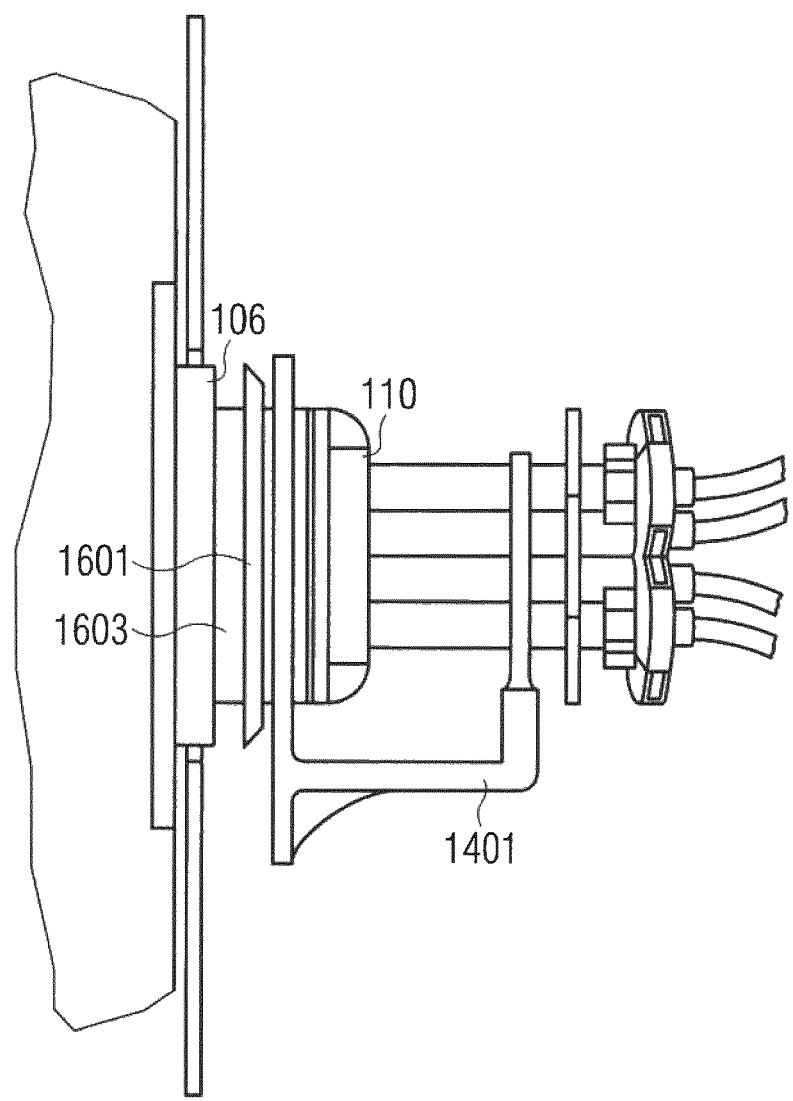
FIG. 16 shows initial placement of the holder on the transfer interface.

FIG. 16 shows the holder 1401 before the holder 1401 has been placed into a final position. In particular, the holder 1401 is depicted upon initial attachment to the transfer interface 110. Place the holder 1401 in the final position may involve sliding the holder hover a radial projection 1601 of the port 106 and into a groove 1603 of the port 106. The groove 1603 may be a radial indentation or recess.

Figure 17:
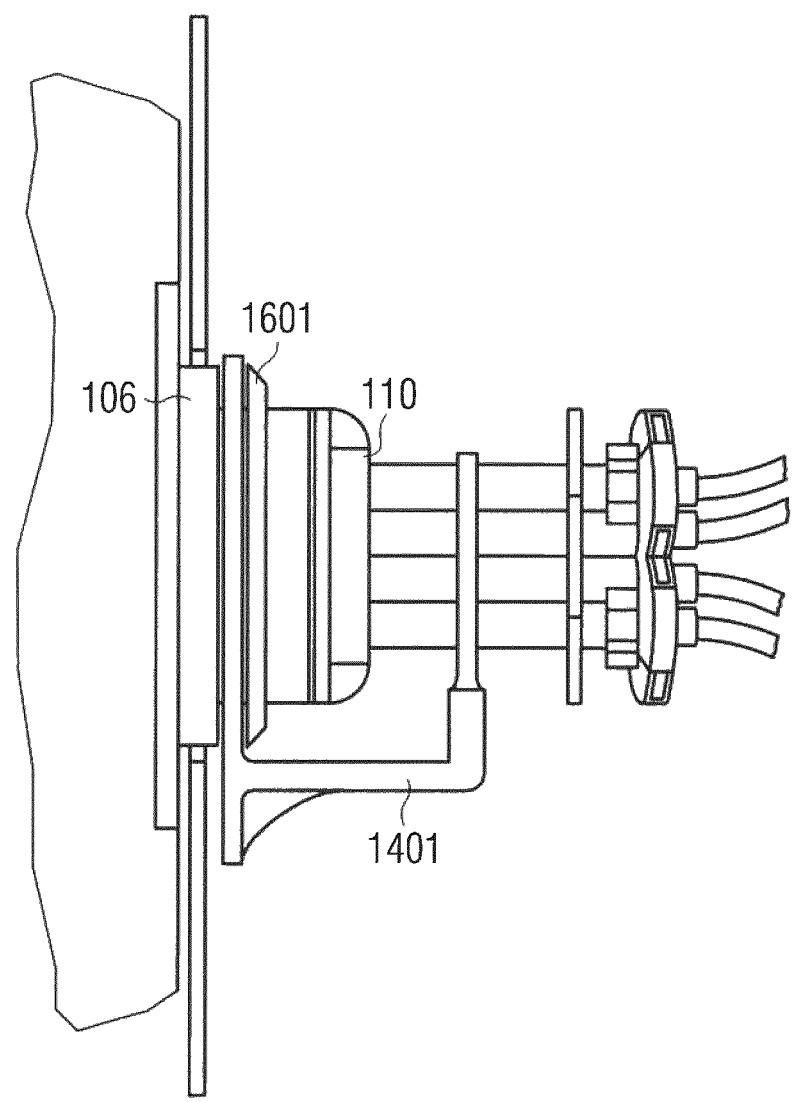
FIG. 17 shows the holder after it has been snapped into place.

FIG. 17 shows the holder 1401 after the holder 1401 has been placed into the final position. In particular, the holder 1401 may be slid along the longitudinal axis of the transfer interface 110, toward the container 102, over the radial projection 1601 to fit into the groove 1603. Accordingly, FIG. 17 shows the holder 1401 after the holder 1401 has been slid over the radial projection 1601 into the groove 1603.

Figure 18:
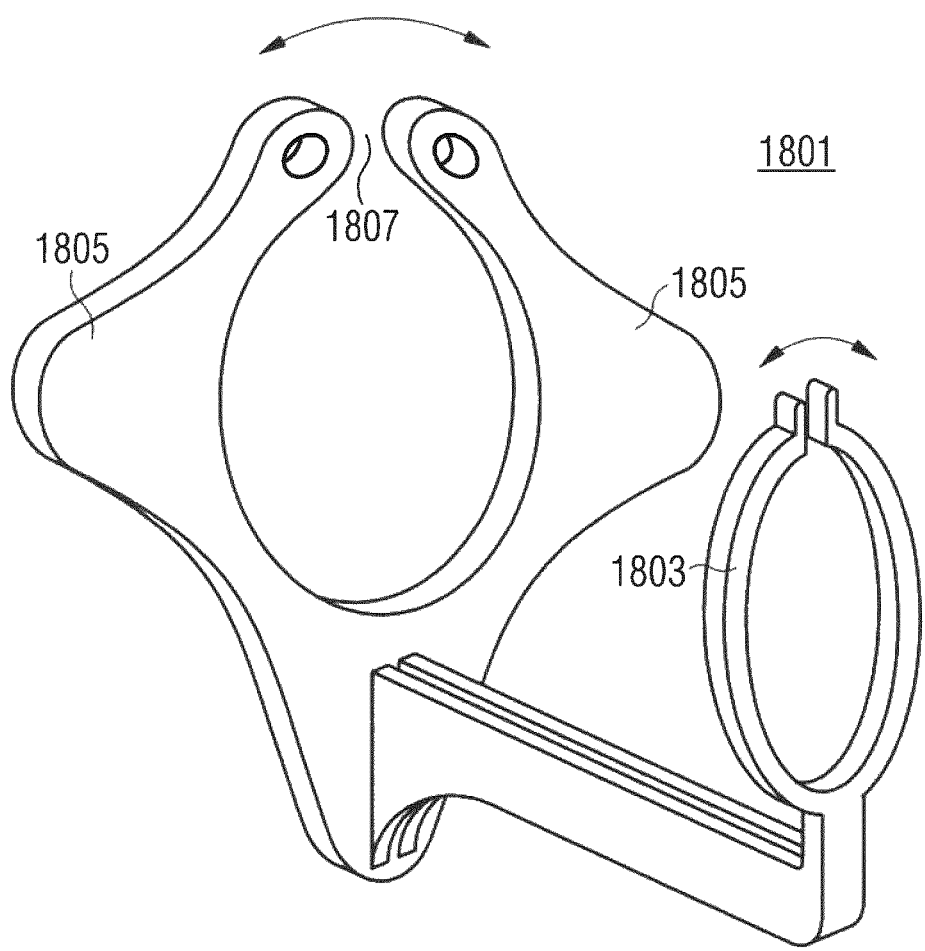
FIG. 18 shows an alternative embodiment of the holder.

FIG. 18 shows another holder 1801. Unless otherwise indicated, the characteristics of the holder 1401 apply to the holder 1801.

The holder 1801 includes lateral extensions 1805. The lateral extensions 1805 may be similar or identical to the lateral extensions 1405. In addition, the holder 1801 includes an attachment 1803. Rather than the ring shape of the attachment 1403, the attachment 1803 has a horseshoe shape. Accordingly, it may be possible to attach the holder 1801 to the transfer interface 110 more easily via the attachment 1803 in comparison to the attachment 1403. In particular, it might not be necessary to detach the distribution tubes 401 or other components of the transfer interface 110 in order to attach the holder 1801.

LIST OF REFERENCE NUMERALS 100 system for transferring chemical, pharmaceutical and/or biological material into or out of a container
102 disposable container
104 housing
106,1101 port
108 opening
110,1100,1210 transfer interface
201 plate
203 holes
204 connecting flange
205 internal flanges
207,1109 O-ring
208 stopping flange
209 containing tube
351 extended transfer element
353 locking mechanism
401 distribution tubes
501 mounting bracket
601 grip
710 multi-use transfer interface
712,1103 triclamp
714 fastening element
716,802 port of multi-use container
1105 supporting protrusion
1107 clamp gasket
1201 connecting protrusion
1203 port flange
1205 stopping protrusion of the port
1207 extending part of the stopping protrusion
1208 stopping flange of the transfer interface
1209 flat portion of the stopping flange
1211 extending portion of the stopping flange
1213 parallel part of the stopping protrusion
1301 junction
1401,1801 holder
1403,1803 attachment
1405,1805 lateral extension
1407,1807 opening
1601 radial projection
1603 groove

The invention claimed is:
1. A system for transferring chemical, pharmaceutical, and/or biological material into or out of a container, the system comprising:

a disposable container having at least one port for accessing an interior of the container, the at least one port including a first port comprising at least one connecting protrusion extending parallel to the container, wherein a surface of the container accessible through the at least one port is made from a flexible material; and a transfer interface connectable to the first port, the transfer interface comprising:
   a plurality of extendible transfer elements adapted to extract one or more samples from the container;
   a plate; and
   at least one connecting flange extending from the plate, the at least one connecting flange configured to be rotated under the at least one connecting protrusion to connect the transfer interface to the first port, such that when the transfer interface is connected to the first port the plate is parallel to the surface of the container,
wherein the plate is convex and adapted to conform to the surface of the container, and the plate at least partly contacts the surface of the container when the transfer interface is connected to the first port.

2. The system of claim 1, wherein the plate is opposite an opening in the container, such that the plate does not contact the surface of the container when the transfer interface is connected to the first port.

3. The system of claim 1, wherein the first port further comprises at least one stopping protrusion extending away from the container, wherein the at least one connecting protrusion extends inward from the at least one stopping protrusion; and
   wherein the system further comprises at least one stopping flange extending from the transfer interface, the at least one stopping flange being located between the plate and an end of the transfer interface opposite the plate, the at least one stopping flange abutting the at least one stopping protrusion when the transfer interface is connected to the first port.

4. The system of claim 3, wherein the at least one stopping flange comprises an extending portion and a flat portion, the extending portion extending radially outward from the flat portion,
   wherein the at least one stopping protrusion comprises an extending part and a parallel part, the extending part extending away from the container, the parallel part extending in a direction parallel to the surface of the container, and
   wherein, when the transfer interface is connected to the first port, the extending portion abuts the parallel part of the stopping protrusion and the flat portion abuts the extending part of the at least one stopping protrusion.

5. The system of claim 1, wherein the at least one connecting flange extends
   radially outward from the plate, wherein at least part of a circumference of the transfer interface is not covered by the connecting flange, the at least one connecting flange being in contact with the surface of the container when the transfer interface is connected to the first port.

6. The system of claim 3, further comprising
   an O-ring located between the connecting flange and the stopping flange.

7. The system of claim 6, further comprising:
   two internal flanges located between the at least one connecting flange and the at least one stopping flange, wherein each of the two internal flanges extends radially outward from the transfer interface and covers an entire circumference of the transfer interface,
      wherein the O-ring is located between the two internal flanges and is supported by
   the two internal flanges.

8. The system of claim 1, wherein the first port comprises a port flange attached to the disposable container.

9. The system of claim 1, wherein the at least one connecting flange comprises two connecting flanges separated by a first gap and a second gap, wherein at least a portion of each of the two connecting flanges can extend around a quarter of a circumference of the plate.

10. The system of claim 9, wherein the two connecting flanges are diametrically opposed and the first and second gaps are diametrically opposed.

11. The system of claim 1, further comprising a holder that supports the transfer interface when the transfer interface is connected to the first port.

12. The system of claim 11, wherein the holder comprises an attachment for the transfer interface in the shape of a ring or a horseshoe.

13. The system of claim 11, wherein the holder comprises lateral extensions that contact the surface of the container when the transfer interface is connected to the first port, wherein the lateral extensions support the transfer interface.

14. The system of claim 12, wherein the holder comprises lateral extensions that contact the surface of the container when the transfer interface is connected to the first port, wherein the lateral extensions support the transfer interface via the attachment for the transfer interface.

* * * * *